(12) United States Patent
Roider et al.

(10) Patent No.: US 9,883,996 B2
(45) Date of Patent: Feb. 6, 2018

(54) METHODS AND COMPOSITIONS FOR ENHANCING SKIN PIGMENTATION

(71) Applicant: THE GENERAL HOSPITAL CORPORATION, Boston, MA (US)

(72) Inventors: Elisabeth Maria Roider, Boston, MA (US); David Erich Fisher, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/942,457

(22) Filed: Nov. 16, 2015

(65) Prior Publication Data

US 2016/0136070 A1 May 19, 2016

Related U.S. Application Data

(60) Provisional application No. 62/079,772, filed on Nov. 14, 2014.

(51) Int. Cl.
| | | |
|---|---|---|
| *A61K 8/41* | (2006.01) | |
| *A61K 31/121* | (2006.01) | |
| *A61K 31/132* | (2006.01) | |
| *A61K 31/7076* | (2006.01) | |
| *A61K 8/35* | (2006.01) | |
| *A61K 8/40* | (2006.01) | |
| *A61K 8/46* | (2006.01) | |
| *A61Q 1/02* | (2006.01) | |
| *A61Q 19/04* | (2006.01) | |
| *A61Q 5/10* | (2006.01) | |
| *A61K 31/155* | (2006.01) | |

(52) U.S. Cl.
CPC ............... *A61K 8/41* (2013.01); *A61K 8/35* (2013.01); *A61K 8/40* (2013.01); *A61K 8/46* (2013.01); *A61K 31/121* (2013.01); *A61K 31/132* (2013.01); *A61K 31/155* (2013.01); *A61K 31/7076* (2013.01); *A61Q 1/02* (2013.01); *A61Q 5/10* (2013.01); *A61Q 19/04* (2013.01)

(58) Field of Classification Search
CPC ........ A61Q 17/04; A61Q 19/00; A61Q 19/04; A61Q 19/08; A61Q 17/00; A61Q 17/02; A61Q 5/10; A61K 2800/522; A61K 2800/94; A61K 8/375; A61K 8/447; A61K 8/46; A61K 8/86; C08G 65/334

See application file for complete search history.

(56) References Cited

U.S. PATENT DOCUMENTS

| | | | |
|---|---|---|---|
| 5,296,500 A | | 3/1994 | Hillerbrand |
| 5,700,450 A | * | 12/1997 | Gilchrest ............... A61K 8/375 424/59 |
| 6,284,258 B1 | | 9/2001 | Rose et al. |
| 2003/0229141 A1 | | 12/2003 | Yu et al. |

FOREIGN PATENT DOCUMENTS

| | | |
|---|---|---|
| EP | 0219455 A2 | 4/1987 |
| EP | 2080504 A2 | 7/2009 |
| WO | 96/00060 A1 | 1/1996 |
| WO | 2014/015118 A1 | 1/2014 |
| WO | 2014/086785 A1 | 6/2014 |

OTHER PUBLICATIONS

Jacoby ("Neonatal Hyperpigmentation: Diagnosis of Familial Glucocorticoid Deficiency with a Novel Mutation in the Melanocortin-2 Receptor Gene", Pediatric Dermatology, vol. 31, No. 1, e13-e17, 2014, cited by Applicant in IDS filed Apr. 7, 2016).*
Meimaridou ("Mutatiosn in NNT encoding nicotinamide nucleotide transhydrogenase cause familial glucocorticoid deficiency", Nature Genetics, vol. 44, No. 7, Jul. 2012, pp. 740-743).*
"Nicotinamide Nucleotide Transhydrogenase (NNT) Links the Substrate Requirement in Brain Mitochondria for Hydrogen Peroxide Removal to the Thioredoxin/Peroxiredoxin (Trx/Prx) System", The Journal of Biological Chemistry, vol. 289, No. 22, pp. 15611-15620, May 2014.*
Freeman et al., "Deletion of Nicotinamide Nucleotide Transhydrogenase: A New Quantitive Trait Locus Accounting for Glucose Intolerance in C57BL/6J mice", Diabetes 55(7):2153-2156 (2006).
Hoek et al., "Comparative studies on nicotinamide nucleotide transhydrogenase from different sources", Biochim Biophys Acta 333(2):237-245 (1974). (Abstract Only).
Ito et al., "Usefulness of alkaline hydrogen peroxide oxidation to analyze eumelanin and pheomelanin in various issue samples: application to chemical analysis of human hair melanins", Pigment Cell Melanoma Research 24 (4):605-613 (2011).
Meadows et al., "A High-Throughput Assay for Modulators of NNT Activity in Permeabilized Yeast Cells", Journal of Biomolecular Screening 16(7):734-743 (2011).
Mitra et al., "An ultraviolet-radiation-independent pathway to melanoma carcinogenesis in the red hair/fair skin background", Nature 491(7424):449-453 (2012). (Author Manuscript).
Moody et al., "Inhibition of nicotinamide nucleotide transhydrogenase in rat liver submitochondrial particles by dicyclohexylcarbodi-imide and butanedione", Biochem. J. 209(3):889-892 (1983).
Rydstrom, "Site-Specific Inhibitors of Mitochondrial Nicotinamide-Nucleotide Transhydrogenase", Eur. J. Biochem. 31(3):496-504 (1972).

(Continued)

*Primary Examiner* — Audrea Buckley
(74) *Attorney, Agent, or Firm* — David S. Resnick; Teresa A. Ptashka; Nixon Peabody LLP

(57) ABSTRACT

Described herein are methods and compositions useful for enhancing pigmentation, such as skin, eye and/or hair pigmentation comprising administering e.g., an NNT inhibitor or an agent that modifies redox status in a melanocyte.

8 Claims, 33 Drawing Sheets

(15 of 33 Drawing Sheet(s) Filed in Color)

(56) References Cited

OTHER PUBLICATIONS

Tada et al., "Scavenging or Quenching Effect of Melanin on Superoxide Anion and Singlet Oxygen", J Clin Biochem Nutr. 46(3):224-228 (2010).

Jacoby et al., "Neonatal Hyperpigmentation: Diagnosis of Familial Glucocorticoid Deficiency with a Novel Mutation in the Melanocortin-2 Receptor Gene", Pediatric Dermatology 31(1):e13-e17 (2014).

Lopert et al., "Nicotinamide Nucleotide Transhydrogenase (Nnt) Links the Substrate Requirement in Brain Mitochondria for Hydrogen Peroxide Removal to the Thioredoxin/Peroxiredoxin (Trx/Prx) System", The Journal of Biological Chemistry 289(22):15611-15620 (2014).

Meimaridou et al., "Mutations in NNT encoding nicotinamide nucleotide transhydrogenase cause familial glucocorticoid deficiency", Nature Genetics 44(7):740-742 (2012).

* cited by examiner

* p < 0.05

N,N-Dicyclohexylcarbodiimide (DCC)

2,3-Butanedione

Palmitoyl-CoA

TOPICAL TREATMENT

DCC 50 mM
2,3-Butanedione 50 mM
DMSO
Palmitoyl-CoA 50 mM

INTRADERMAL TREATMENT

DMSO
Palmitoyl-CoA 50 mM

*p < 0.05

U257, 3d after DCCD

WM26, 3d after DCCD

*$p < 0.05$

* p < 0.05

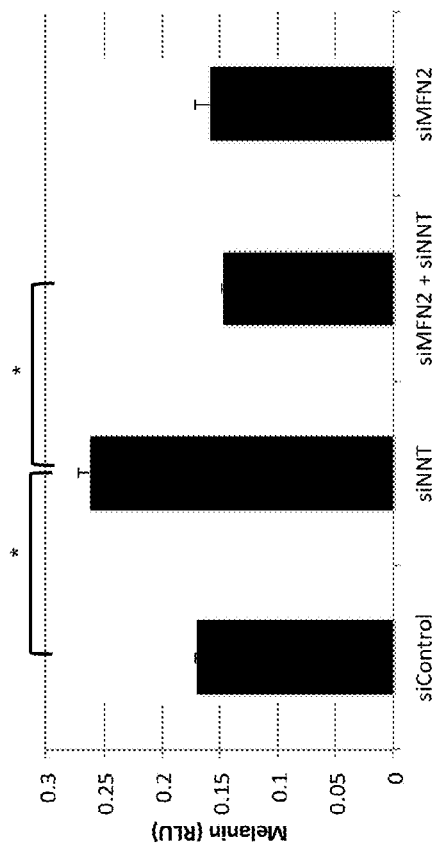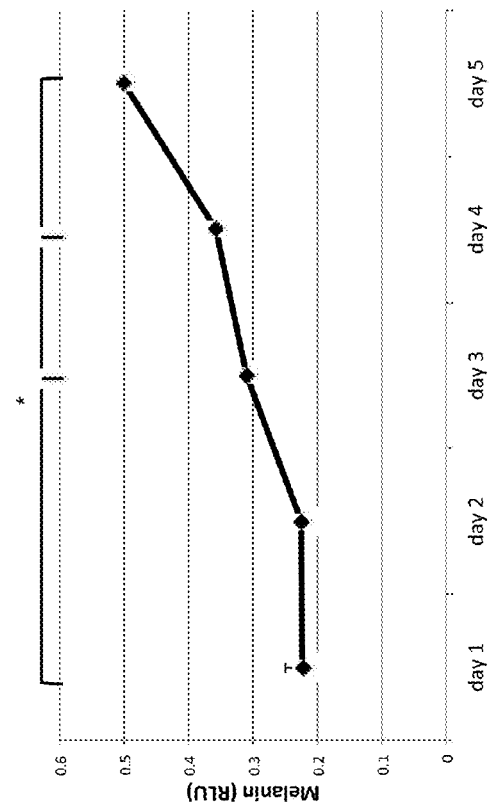
FIG. 14A
FIG. 14B
* $p < 0.05$ $p < 0.05$

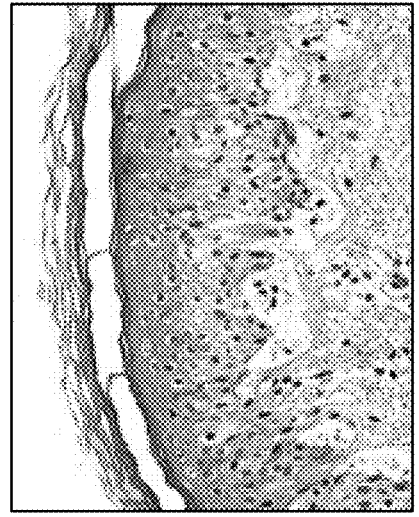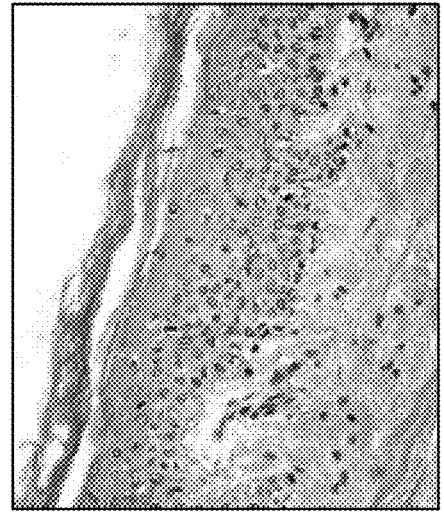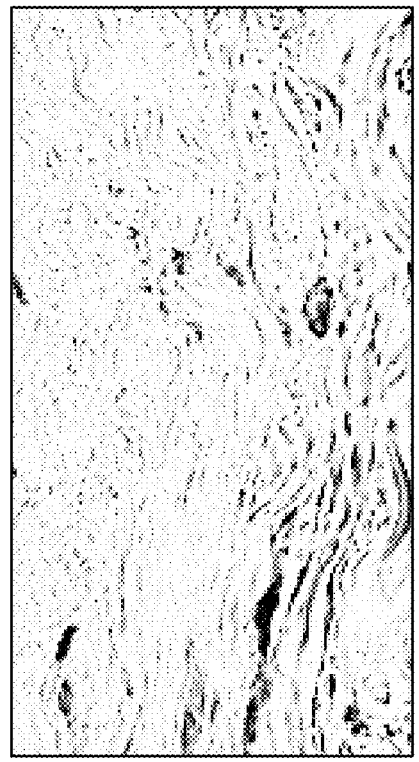
FIG. 21A  FIG. 21B

FIG. 26A

Red Mc1R e/e mice

MiWhite +/- mice

METHODS AND COMPOSITIONS FOR ENHANCING SKIN PIGMENTATION

CROSS-REFERENCE TO RELATED APPLICATIONS

This Application claims benefit under 35 U.S.C. 119(e) of U.S. Provisional Application No. 62/079,772 filed Nov. 14, 2014, the contents of which are incorporated herein by reference in its entirety.

FIELD OF THE INVENTION

The field of the invention relates to the inhibition of nicotinamide nucleotide transhydrogenase (NNT) for enhancing skin and/or hair pigmentation.

BACKGROUND

Skin color variations are probably the most obvious difference within humans. It is known that the transcription factor MITF controls skin pigmentation by regulating the transcription of various pigmentation genes, such as TRP1, TRP2, and TYR. Altogether these genes alter the Pheomelanin (red pigment) to Eumelanin (black pigment) ratio of pigmented cells resulting in differently pigmented human skin. It is well known that skin types differ depending on the human's environment due to two reasons: Sufficient protection of UV light and Vitamin D production. Both factors are necessarily inversely correlated. Being perfectly adapted to their original habitat, the migration of people increased their risk of being maladapted and to develop skin cancer or Vitamin D deficiency.

Additionally, hyper- or hypopigmentary disorders are extremely common in the human population. Whereas minor, local changes are often well tolerated and accepted, major diseases usually display as disfiguring body condition with very limited treatment options.

SUMMARY

The methods and compositions provided herein are based on the discovery that modification of the reduction/oxidative status of a cell (e.g., a melanocyte) by inhibition of nicotinamide nucleotide transhydrogenase (NNT) enhances skin pigmentation. Thus, modulating the cutaneous pigmentation via modification of such a specific redox-system mechanism can be used to prevent melanoma formation and to treat pigmentation disorders.

In one embodiment, one of skill in the art directly modulates the cutaneous eumelanin to pheomelanin ratio via a specific and efficient alteration of the enzyme NNT. Such methods offer an exciting new strategy towards reducing melanoma risk, as well as new options to treat various pigmentation disorders of human skin, hair, and eyes. It will be understood by one of skill in the art that both cosmetic and therapeutic increases in skin pigmentation will protect the subject from a host of skin cancers and/or associated sun damage. For example, the methods and compositions provided herein can provide protection from general DNA damage, basal cell carcinoma, squamous cell carcinoma, melanoma, malignant melanoma, actinic keratosis, Kaposi's sarcoma, Bowen's disease, and merkel cell carcinoma. In other embodiments, the methods and compositions provided herein, in addition to enhancing skin, eye and hair pigmentation, can also provide protection from sun-induced damage and other cosmetic concerns including, for example, DNA damage, seborrheic keratosis, moles, wrinkles, liver or age spots, skin sagging, bags under the eyes, loss of skin elasticity, uneven skin tone, freckles, melasma (e.g., mask of pregnancy), actinic cheilitis, cataracts, etc.

Described herein are methods and compositions useful for enhancing pigmentation, such as skin, eye and/or hair pigmentation comprising administering e.g., an NNT inhibitor or an agent that modifies redox status in a melanocyte.

One aspect described herein relates to a method for enhancing hair and/or skin pigmentation in a subject, the method comprising: administering a composition comprising an inhibitor of nicotinamide nucleotide transhydrogenase (NNT) to a subject in need thereof, thereby enhancing hair and/or skin pigmentation.

In one embodiment of this aspect and all other aspects provided herein, the method further comprises a step of measuring expression of eumelanin, cell viability, or assessing the degree of pigmentation in an area of the hair, skin, or eye to be treated.

In another embodiment of this aspect and all other aspects provided herein, the step of measuring expression of eumelanin is performed by measuring OD 450 nm.

In another embodiment of this aspect and all other aspects provided herein, administering the composition is used to treat and/or prevent a disease, for example, melanoma, basal cell carcinoma, squamous cell carcinoma, melanoma, malignant melanoma, actinic keratosis, Kaposi's sarcoma, Bowen's disease, and merkel cell carcinoma.

In another embodiment of this aspect and all other aspects provided herein, administering the composition is used for cosmetic applications. In other embodiments, the methods and compositions provided herein, in addition to enhancing skin, eye and hair pigmentation, can also provide protection from sun-induced damage and other cosmetic concerns including, for example, DNA damage, seborrheic keratosis, moles, wrinkles, liver or age spots, skin sagging, bags under the eyes, loss of skin elasticity, uneven skin tone, freckles, melasma (e.g., mask of pregnancy), actinic cheilitis, cataracts, etc.

In another embodiment of this aspect and all other aspects provided herein, the cosmetic application comprises sunless tanning, temporary tattooing, modification of eye color, or darkening of hair. It will be appreciated by those of skill in the art that such cosmetic applications to darken skin pigmentation can also provide protection against a variety of skin cancers, skin lesions, DNA damage, or sun-associated skin damage or aging.

In another embodiment of this aspect and all other aspects described herein, the method further comprises a step of determining redox status in a biological sample obtained from the subject.

In another embodiment of this aspect and all other aspects described herein, the redox status is determined by measuring reactive oxygen species (ROS) levels, NAD+/NADH ratios, GSH/GSSG ratios, cell viability, or eumelanin expression.

In another embodiment of this aspect and all other aspects described herein, cell viability is measured using a BrdU assay or ATP-based measurements.

In another embodiment of this aspect and all other aspects described herein, the subject comprises at least one region of hypopigmentation. For example, the subject can comprise vitiligo or similar.

In another embodiment of this aspect and all other aspects described herein, the levels of reactive oxygen species in a biological sample obtained from the subject following treatment with the NNT inhibitor are increased by at least 10% as compared to the levels of reactive oxygen species in a reference sample. In one embodiment, the levels of reactive oxygen species are increased shortly after administration. NNT inhibitors decrease GSH/GSSG levels, in turn causing an increase in reactive oxygen species, only shortly after treatment. Without wishing to be bound by theory, this temporary increase in mitochondrial and/or melanosomal reactive oxygen species, which also causes a decrease in GSH, NADP, and NAD, in turn induces an increase in eumelanin synthesis and thus pigmentation of the cells and/or human skin explants. Without wishing to be bound by theory, this may be due to decreasing cysteine stores, which are needed to form pheomelanin and by increasing tyrosinase protein stability via altering the redox status. Eumelanin is thought to be the most potent reactive oxygen species scavenge, thereby decreasing cellular reactive oxygen species and thus reducing the risk of melanoma formation or other cancer formation. Typically, the redox measurements described herein are a measure of whether an inhibitor is working, however after longer treatment intervals an overall decrease in the amount of reactive oxygen species is observed after inhibition of NNT.

In another embodiment of this aspect and all other aspects described herein, the reference sample comprises a biological sample obtained from the same subject prior to treatment with the NNT inhibitor.

In another embodiment of this aspect and all other aspects described herein, the inhibitor of NNT is administered topically, intradermally, or subcutaneously.

In another embodiment of this aspect and all other aspects described herein, the NNT inhibitor comprises palmitoyl CoA or a derivative thereof.

In another embodiment of this aspect and all other aspects described herein, the NNT inhibitor comprises N, N-Dicyclohexylcarbodiimide (DCC) or a derivative thereof.

In another embodiment of this aspect and all other aspects described herein, the NNT inhibitor comprises 2,3-butanedione (2,3BD) or a derivative thereof.

In another embodiment of this aspect and all other aspects described herein, the NNT inhibitor modifies redox status in a melanocyte of the subject.

Also provided herein in another aspect are methods for enhancing skin or hair pigmentation in a subject, the method comprising administering a composition comprising an agent that modifies redox status in a melanocyte to a subject in need thereof.

In one embodiment of this aspect and all other aspects described herein, the method further comprises a step of determining redox status in a biological sample obtained from the subject.

In another embodiment of this aspect and all other aspects described herein, the redox status is determined by measuring reactive oxygen species (ROS) levels, NAD+/NADH ratios, GSH/GSSG ratios, cell viability, or eumelanin expression.

In another embodiment of this aspect and all other aspects described herein, cell viability is measured using a BrdU assay.

In another embodiment of this aspect and all other aspects described herein, the ratio of reduced glutathione (GSH) to oxidized glutathione (GSSG) is decreased by at least 10% compared to a reference sample.

In another embodiment of this aspect and all other aspects described herein, the ratio of oxidized nicotine adenine dinucleotide (NADH) to reduced nicotine adenine dinucleotide (NAD+) is increased by at least 10% compared to a reference sample.

In another embodiment of this aspect and all other aspects described herein, the ratio of oxidized nicotine adenine dinucleotide phosphate (NADPH) to reduced nicotine adenine dinucleotide phosphate (NADP+) is increased by at least 10% compared to a reference sample.

In another embodiment of this aspect and all other aspects described herein, the GSH/GSSG ratio is less than 10 as determined using an assay comprising GSH/GSSG-GLO assay.

In another embodiment of this aspect and all other aspects described herein, the GSH/GSSG ratio of melanocytes treated with the agent is reduced by at least 20% (e.g., at least 30%, at least 40%, at least 50%, at least 75%, at least 1-fold, at least 2-fold, at least 5-fold, at least 10-fold, at least 100-fold, or more) compared to the GSH/GSSG ratio of untreated melanocytes.

In another embodiment of this aspect and all other aspects described herein, eumelanin expression is increased by at least 5% as measured using O.D. 450 nm.

Another aspect provided herein relates to a method for treating and/or preventing a lesion in a subject, the method comprising administering a composition comprising an inhibitor of nicotinamide nucleotide transhydrogenase (NNT) to a subject in need thereof, thereby treating or preventing the lesion in the subject.

In one embodiment of this aspect and all other aspects provided herein, the lesion comprises a cancerous lesion. Such cancerous lesions can comprise basal cell carcinoma, squamous cell carcinoma, melanoma, malignant melanoma, actinic keratosis, Kaposi's sarcoma, Bowen's disease, and merkel cell carcinoma.

In another embodiment of this aspect and all other aspects provided herein, the cancerous lesion comprises melanoma.

In another embodiment of this aspect and all other aspects provided herein, the method further comprises a step of assessing DNA damage in the lesion.

In another embodiment of this aspect and all other aspects provided herein, the DNA damage in the lesion is assessed by measuring cyclobutane pyrimidine dimers (CPD) in the subject.

In another embodiment of this aspect and all other aspects provided herein, the method further comprises a step of measuring expression of eumelanin in the lesion or area to be treated.

In another embodiment of this aspect and all other aspects provided herein, the step of measuring expression of eumelanin is performed by measuring OD 450 nm.

In another embodiment of this aspect and all other aspects provided herein, the composition is applied as a prophylactic to prevent formation of a lesion.

In another embodiment of this aspect and all other aspects provided herein, the composition is applied to a discrete lesion. Alternatively, the composition can be applied over the entire body.

In another embodiment of this aspect and all other aspects provided herein, the inhibitor of NNT is administered topically, intradermally, or subcutaneously.

In another embodiment of this aspect and all other aspects provided herein, the NNT inhibitor comprises palmitoyl CoA.

In another embodiment of this aspect and all other aspects provided herein, the NNT inhibitor comprises N, N-Dicyclohexylcarbodiimide (DCC) or a derivative thereof.

In another embodiment of this aspect and all other aspects provided herein, wherein the NNT inhibitor comprises 2,3-butanedione.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3A, Measurement of eumelanin via measuring its absorption at 450 nm (OD450) in human SK30 melanoma cells. Low MITF (after 5 days of siNNT treatment) induces pigmentation of UACC257 cells via a N-Acetylcysteine and tyrosinase dependent mechanism. FIG. 3B, Measurement of eumelanin via measuring its absorption at 450 nm (OD450) in UACC257 human melanoma cells. Low MITF (after 5 days of siNNT treatment) induces pigmentation of UACC257 cells via tyrosinase dependent mechanism. *, indicate significant differences ($p<0.05$).

FIG. 6A, Topical treatment of DCC or 2,3 BD showed significant darkening after 5 days of daily application. FIG. 6B, Palmitoyl-CoA, a large molecule, was unable to penetrate after topical application but induced darkening after intradermal treatment of human skin explants.

FIG. 7A, GSH and GSSG measurements in UACC257 melanoma cells. FIG. 7B, GSH and GSSG measurements in primary melanocytes (PM) WM26 cells. FIG. 7C, GSH/GSSG ratios of UACC257 melanoma and WM2 primary melanocytes. *, indicates significant differences ($p<0.05$).

FIGS. 14A-14B show data relating to melanin levels in treated UACC257 melanosomes. FIG. 14A, a bar graph depicting levels of melanin in control and siRNA-treated melanoma cells. NNT is known to be localized in mitochondria and it has been shown that mitochondria and melanosomes are connected via membrane-membrane interaction expression of the gene MFN2 (Daniele et al, Current Biology, 2014). To prove that NNT-mediated redox changes in mitochondria are exchanged via MFN2 with melanosomes, a double silencing experiment was performed. It has been shown that overexpressing NQO1 (which catalyzes the reaction form NADPH→NADP+) impacts tyrosinase protein stability but not mRNA levels, thereby increasing melanin formation and increased pigmentation. A similar effect was suspected for silencing NNT (a gene localized in the inner mitochondrial membrane transferring H+ to NADP+ generating NADPH). FIG. 14B, Liposomal transfection of siRNA targeting NNT (siNNT) gradually induces an increase in pigmentation of intermediately pigmented human UACC257 melanoma cells after 5 days (Note: melanoma cells were used as a model system as those are intermediately pigmented. Human primary melanocytes are completely black and therefore not useful for this type of experiment). *, indicates significant differences ($p<0.05$).

FIG. 20A, A picture of 2,3 Butanedione and DCC treated skin explants (1× per day for 5 consecutive days) showing a visible increase of human skin pigmentation with treatment. FIG.

Figure 1:
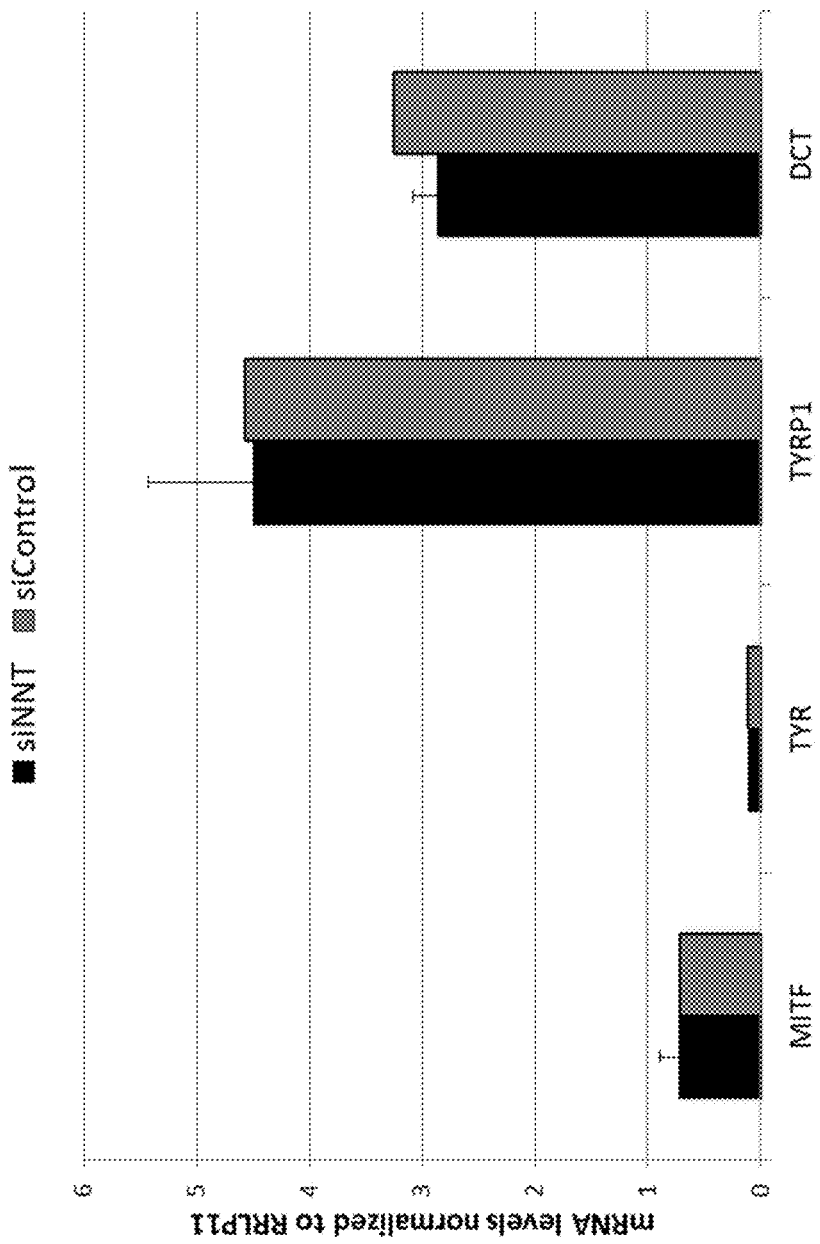
FIG. 1 is a bar graph indicating that the pigmentation change is not due to changes in MITFDCT, TYRP1, or tyrosine mRNA levels.
Figure 2:
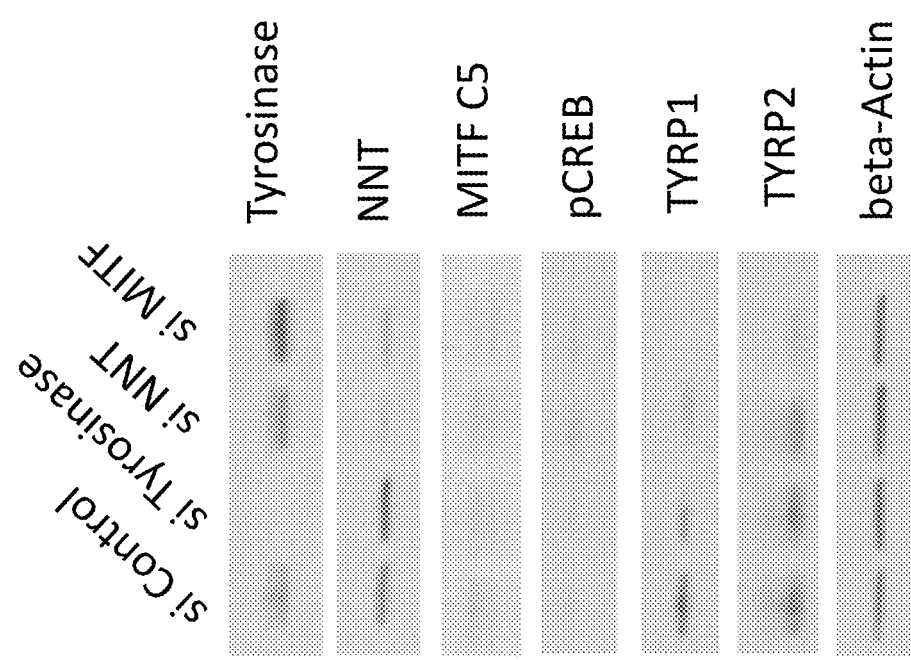
FIG. 2 shows protein levels of tyrosinase, NNT, MITF C5, pCREB, TYRP1, TYRP2 and beta actin in UACC257 melanoma cells.
Figure 3A:
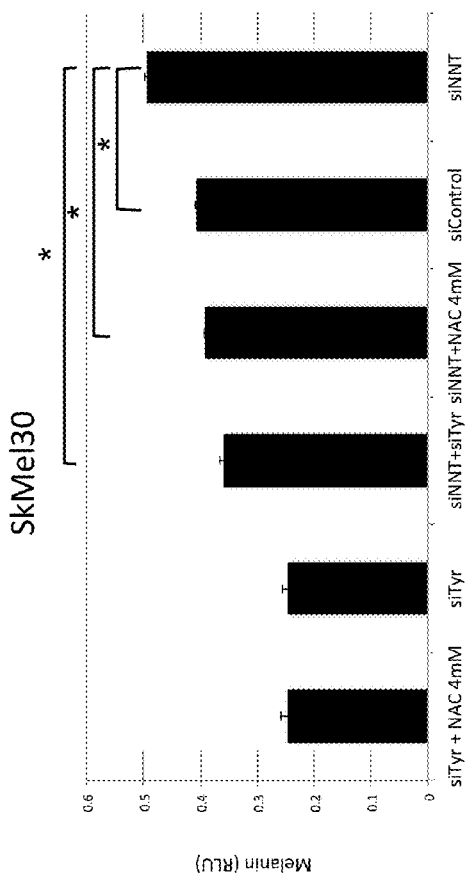
FIGS. 3A-3B show data for eumelanin measurements indicating that NNT-mediated pigment change is cysteine and tyrosinase dependent. Melanoma cells were used due to their intermediate level of pigmentation. Melanocytes are completely black.
Figure 3B:
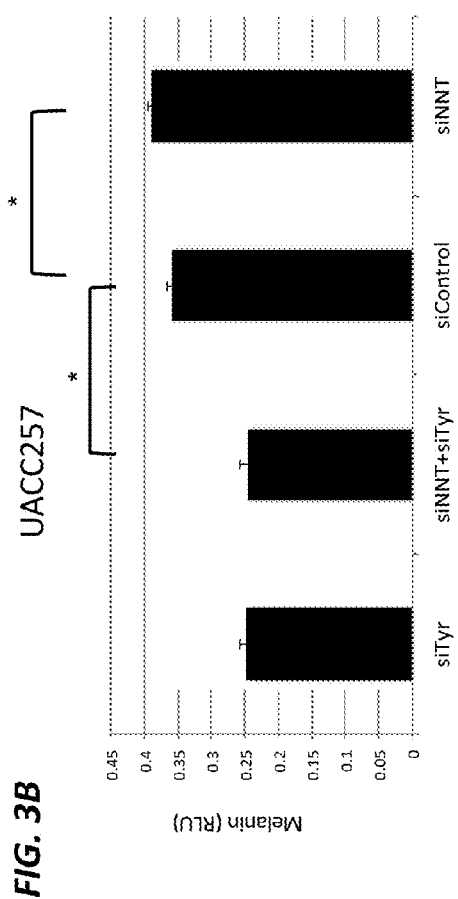
Figure 4:
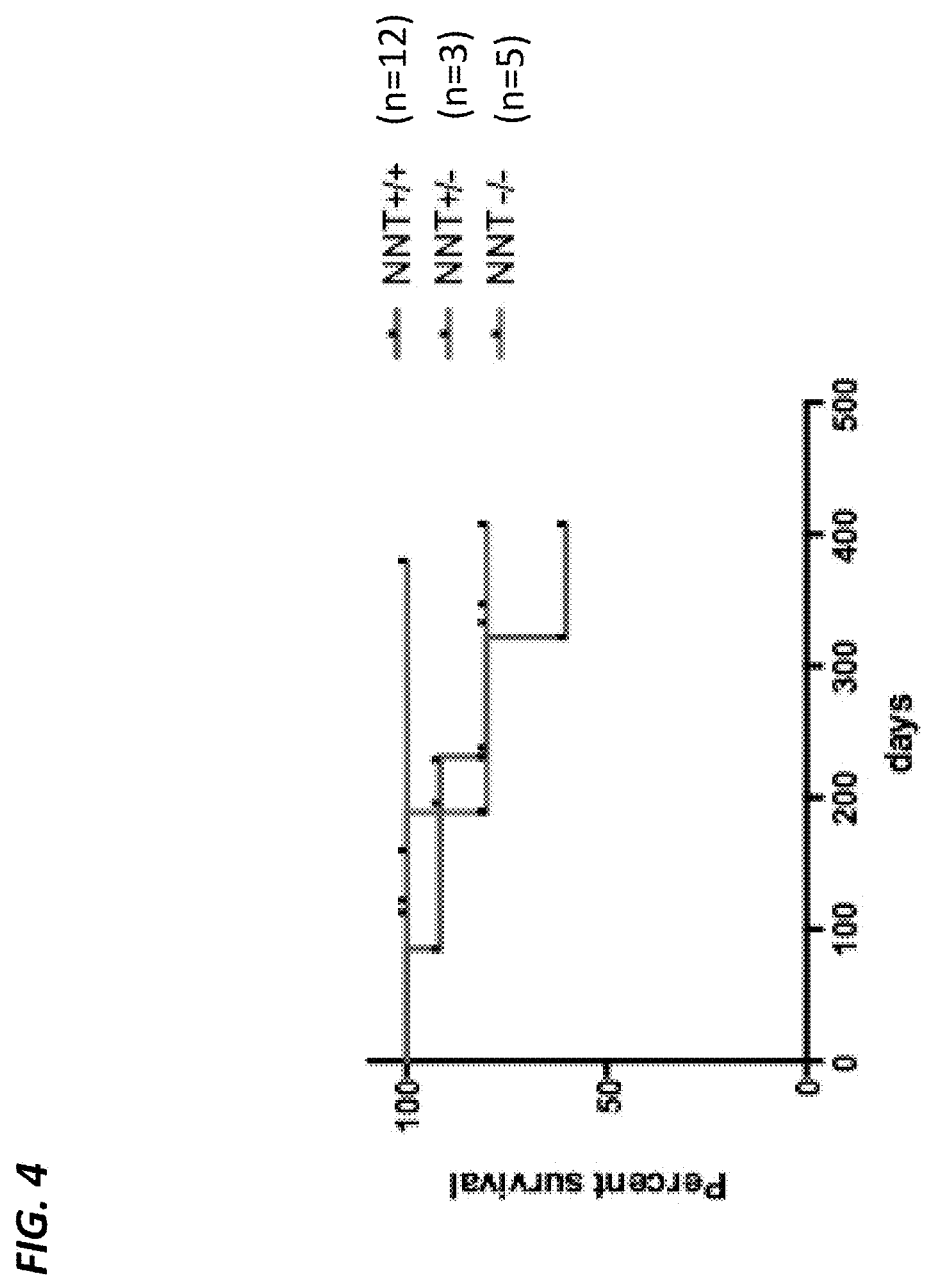
FIG. 4 is a line graph indicating that NNT does not impact survival of mice.
Figure 5:
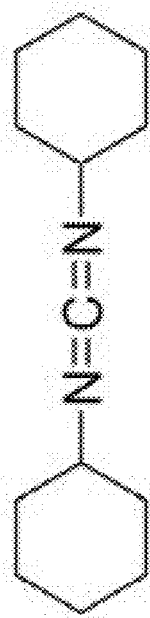
FIG. 5 shows representative site-specific NNT inhibitors.
Figure 5:
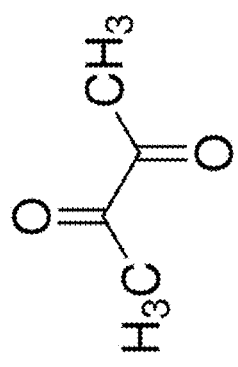
Figure 5:
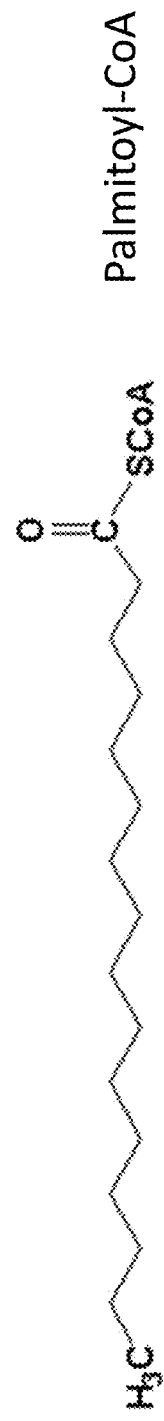
Figure 6A:
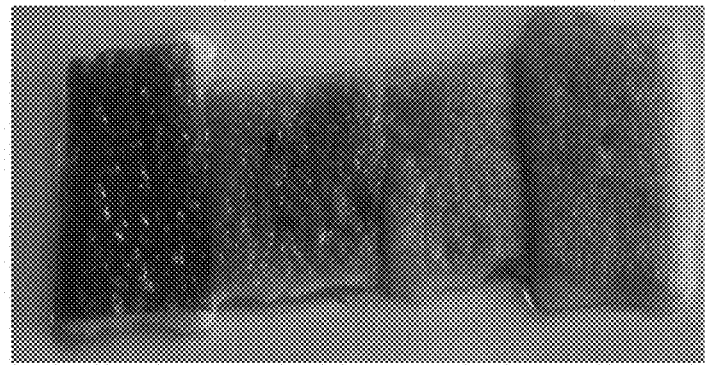
FIGS. 6A-6B show the effect of topical (FIG. 6A) and intradermal (FIG. 6B) treatment of skin with NNT inhibitors.
Figure 6B:
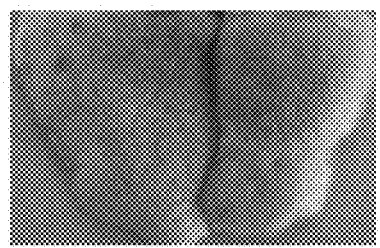
Figure 7A:
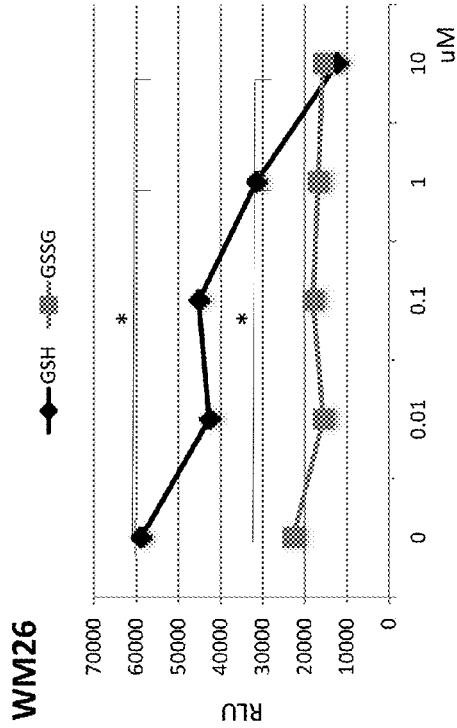
FIGS. 7A-7C show GSH/GSSG ratios 3 days after N,N-Dicyclohexylcarbodiimide (DCC) treatment. To confirm the observation by Moody et al. (Biochem J., 1983) that DCC and Butanedione inhibit NNT enzyme activity, GSH/GSSG measurements were performed in human melanoma and primary melanocytes. These data confirm that the GSH/GSSG ratios (and especially the major antioxidant GSH) decreased in a dose-dependent manner after application of DCC.
Figure 7B:
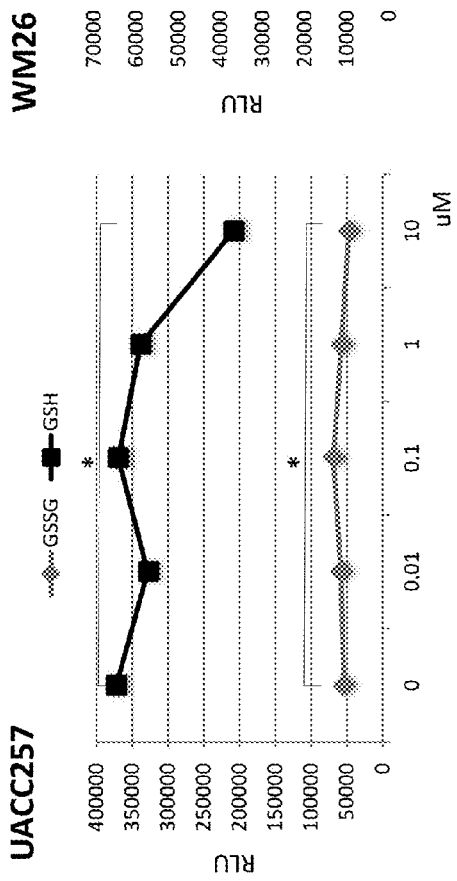
Figure 7C:
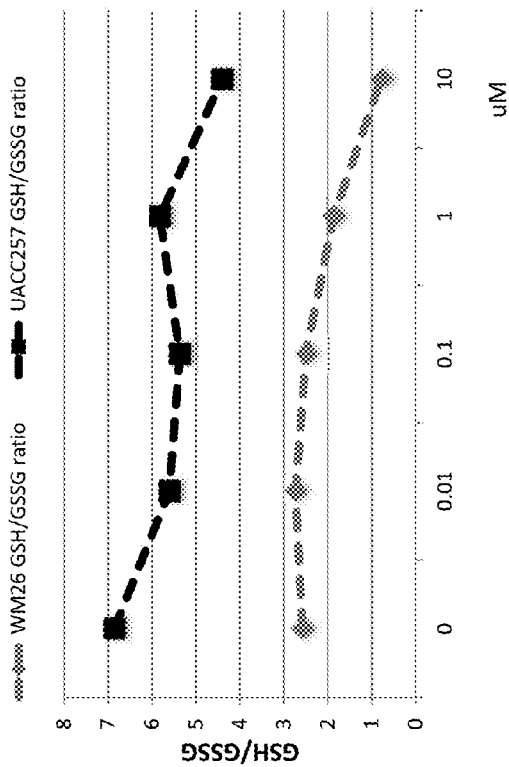
Figure 8A:
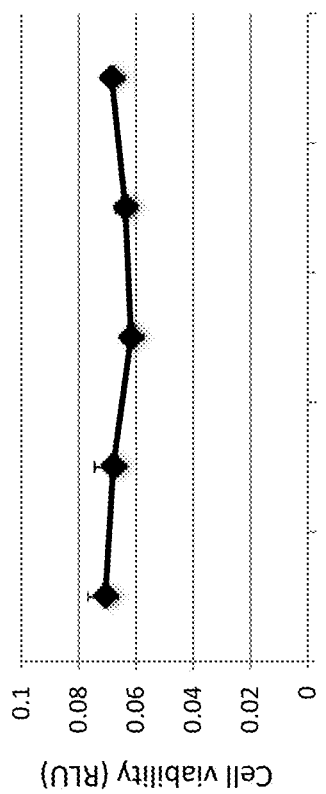
FIGS. 8A-8B show BrdU ELISA data 3 days after DCC treatment. Toxicity of DCC in human UACC 257 melanoma (FIG. 8A) and WM26 primary melanocytes (FIG. 8B) (BRDU measurements) showing no significant induction of cell death.
Figure 8B:
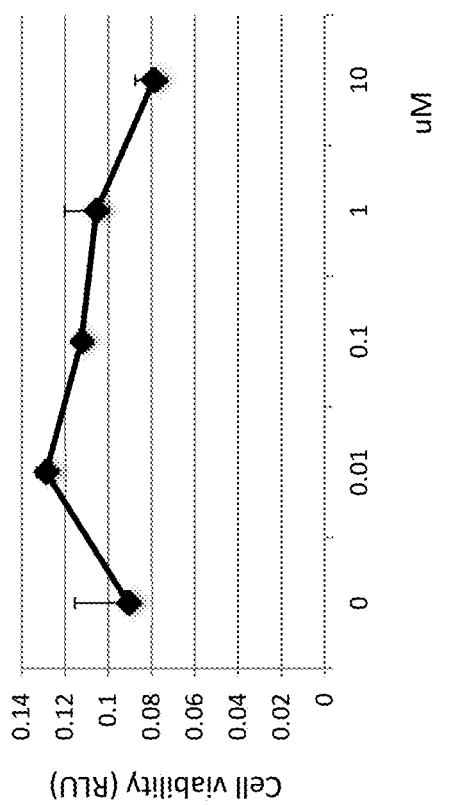
Figure 9:
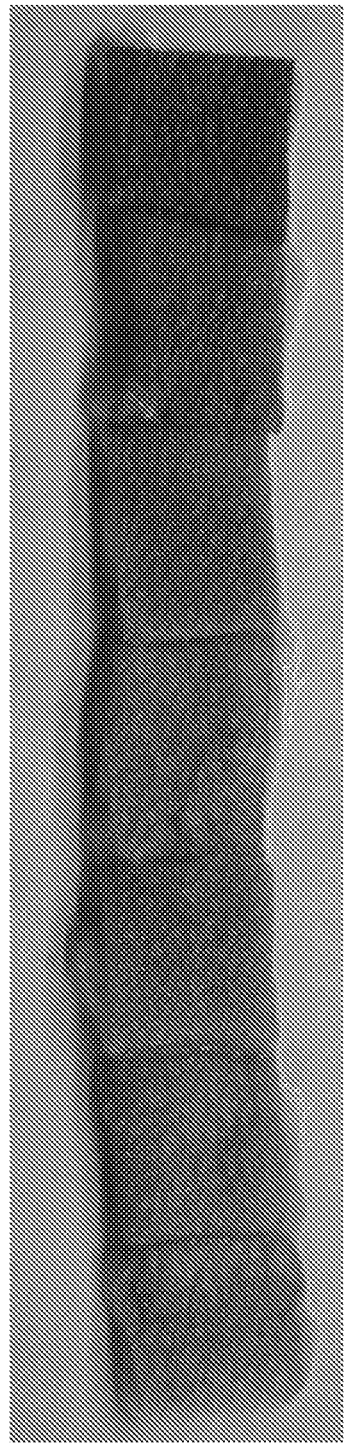
FIG. 9 shows the effect of DCC dose titration on skin pigmentation.
Figure 10:
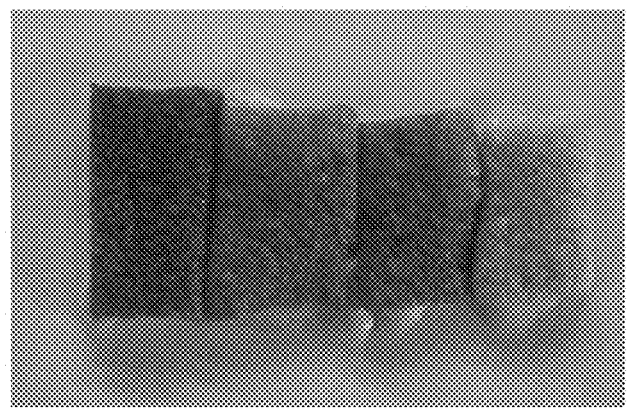
FIG. 10 shows the effect of DCC time titration in human skin.
Figure 11:
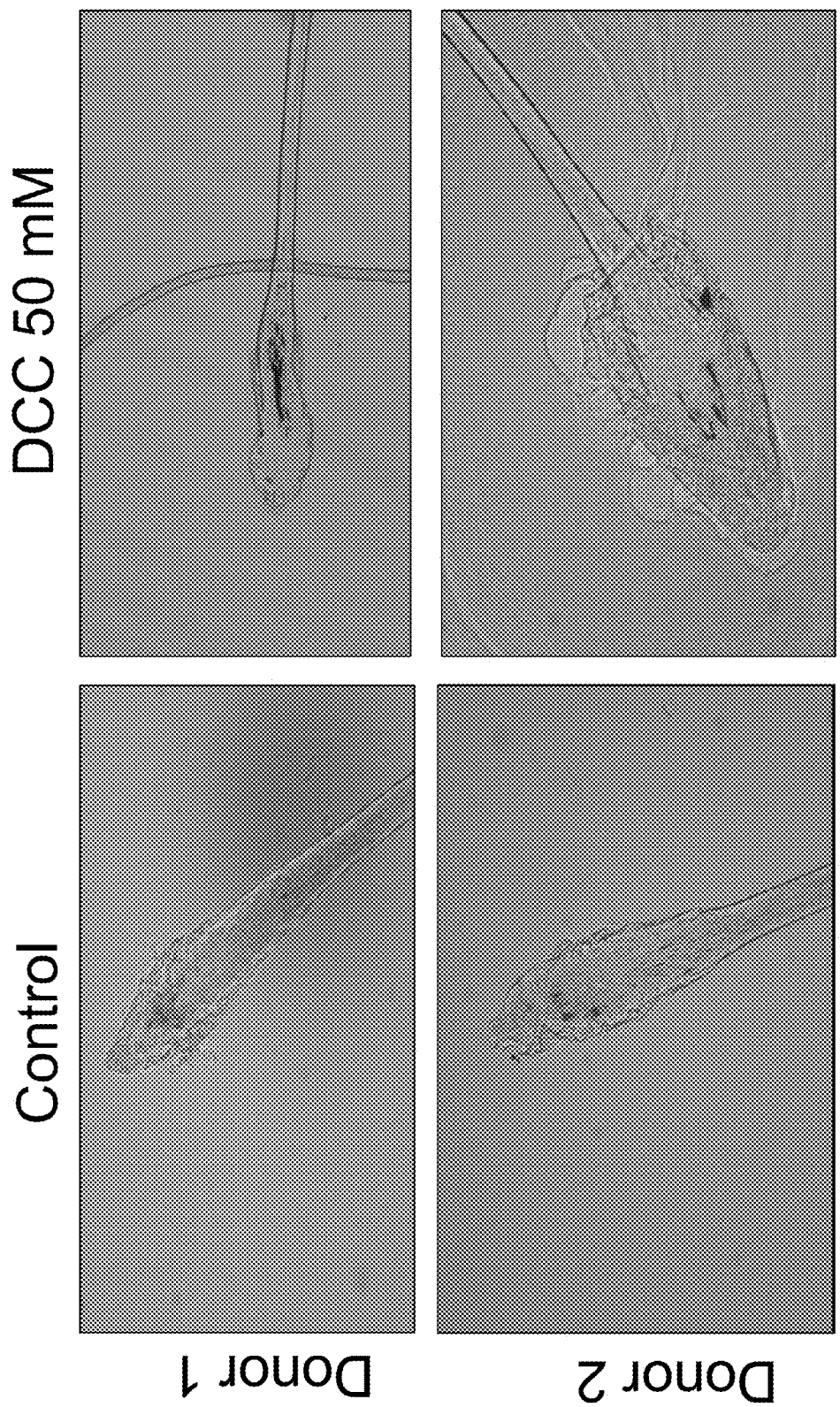
FIG. 11 shows images of hair pigmentation from different human skin grafts in nude mice. The left panel shows hair pigmentation in untreated grafts, while the right panel shows hair pigmentation in grafts treated topically with 50 mm DCC. These data show that human hair (grown on a human skin explant in immunosuppressed SCID mice) has increased pigmentation after 12 days of daily treatment (weekdays) with 50 mM DCC as compared to control treated animals (DMSO).
Figure 12:
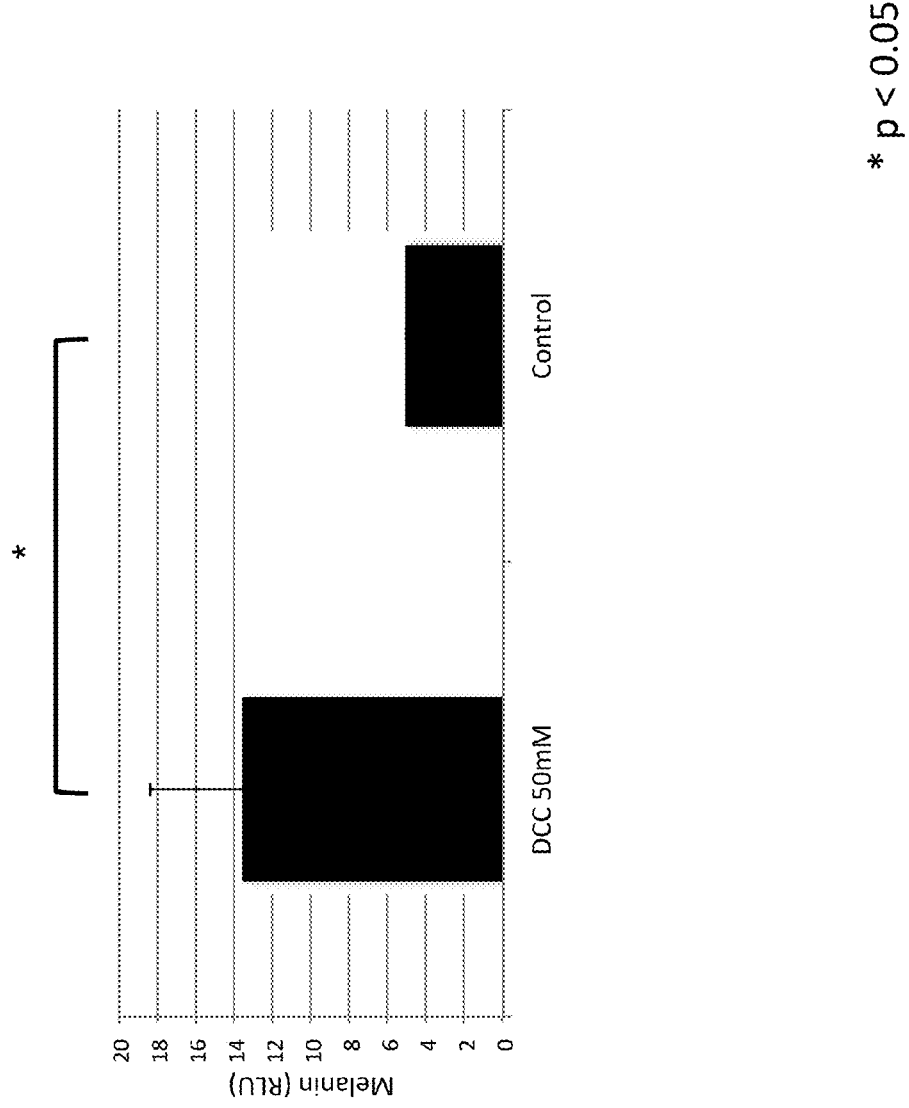
FIG. 12 shows the quantification of pigmentation from the human skin grafts of FIG. 11. *, indicates significant differences ($P<0.05$).
Figure 13:
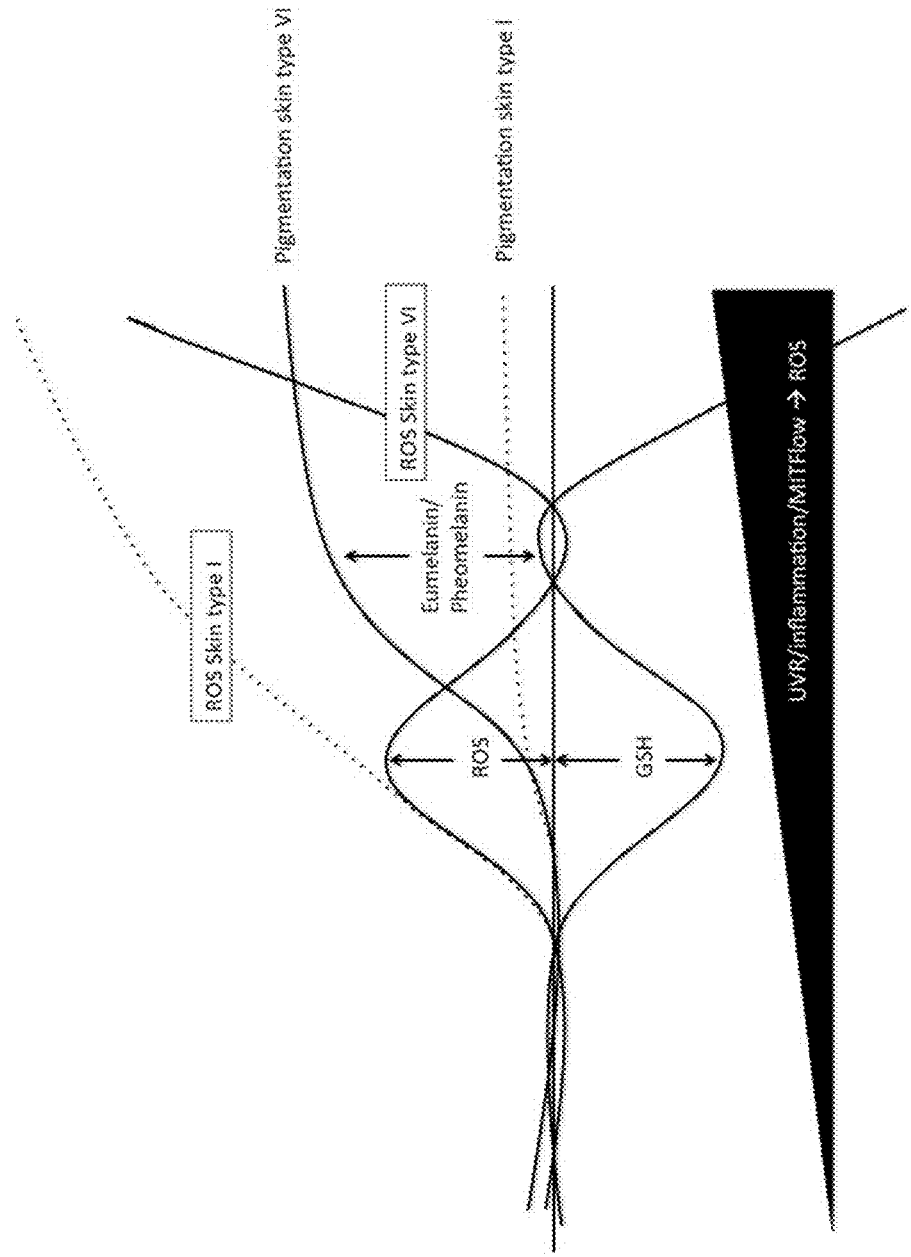
FIG. 13 shows a schematic depicting the balance between ROS generation and skin pigmentation and their impact on protecting human skin.
Figure 15:
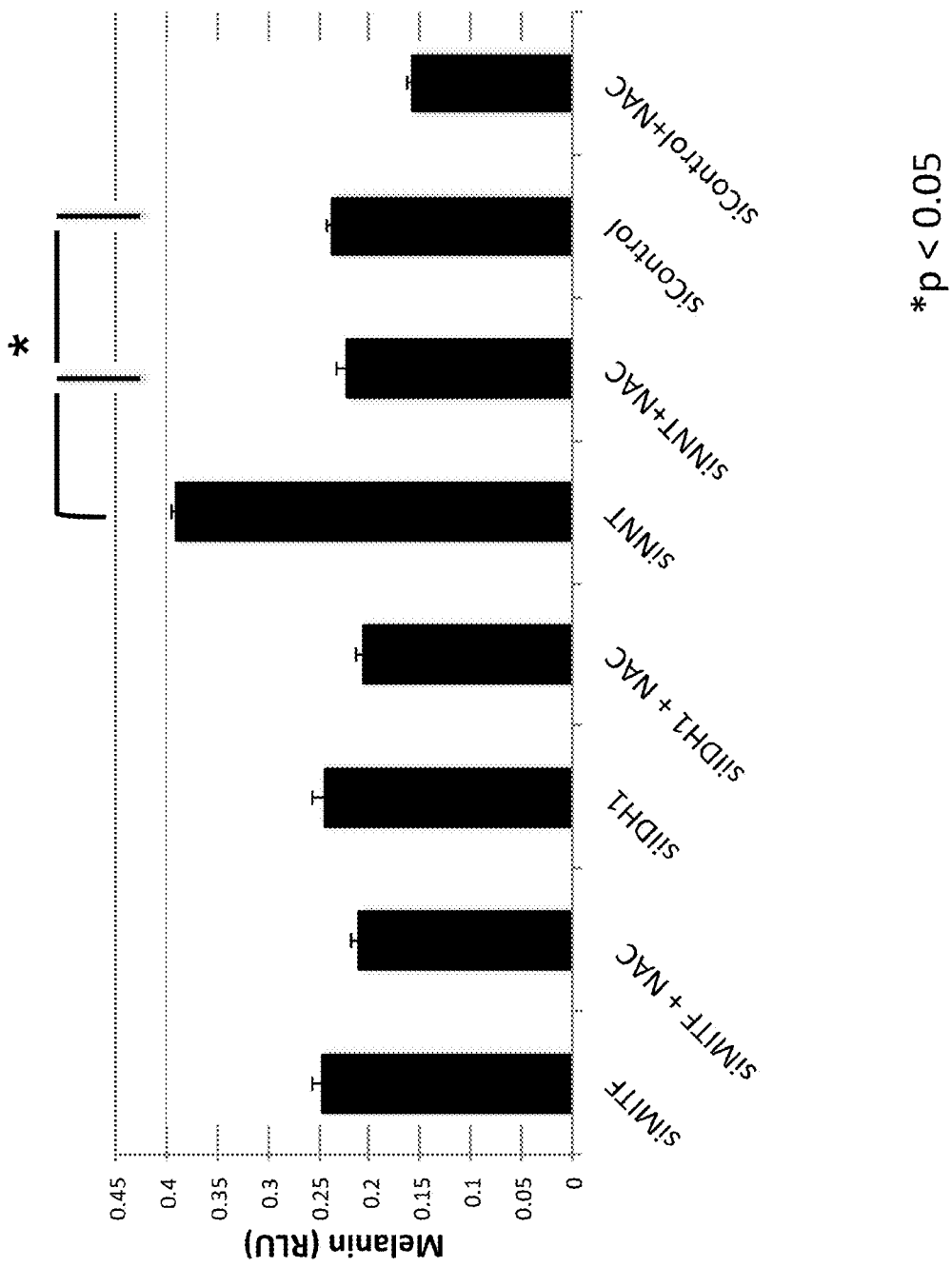
FIG. 15 shows data related to the measurement of eumelanin via measuring its absorption at 450 nm (OD450) in human UACC257 melanoma cells. These data indicate that low MITF (after 5 days of siNNT treatment) induces pigmentation of UACC257 cells via a N-Acetylcysteine dependent mechanism. Effects of two other genes involved in redox changes (MITF, IDH1) were measured, showing that the pigmentation-inducing effect is specific to siNNT. siNNT levels are significantly higher than all other treatment arms ($p<0.05$). *, indicates significant differences ($p<0.05$).
Figure 16:
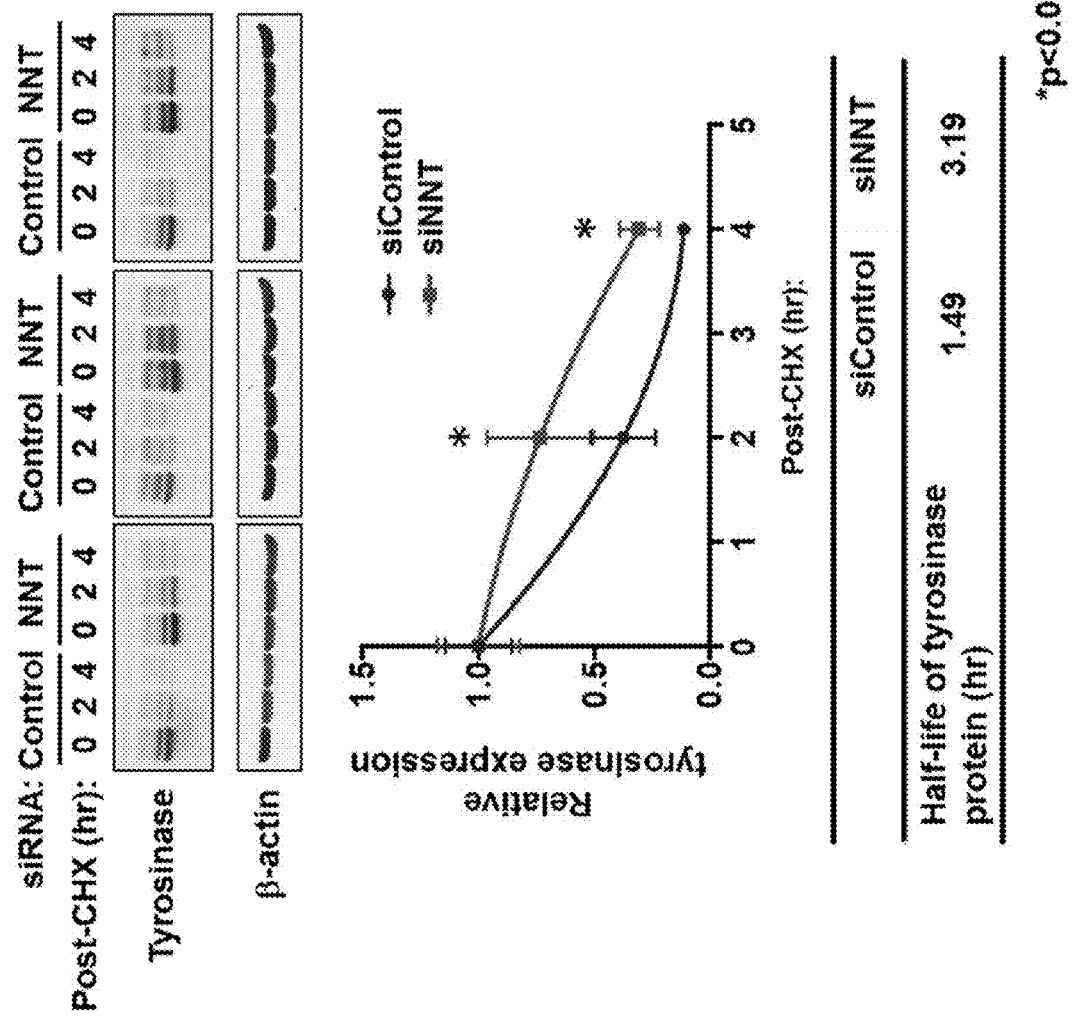
FIG. 16 shows data from a tyrosinase protein stability assay. NNT silencing significantly stabilizes tyrosinase protein. Measurements were performed in UACC257 melanoma cells 3 days post siRNA transfection. *, indicates significant differences ($p<0.05$).
Figure 17:
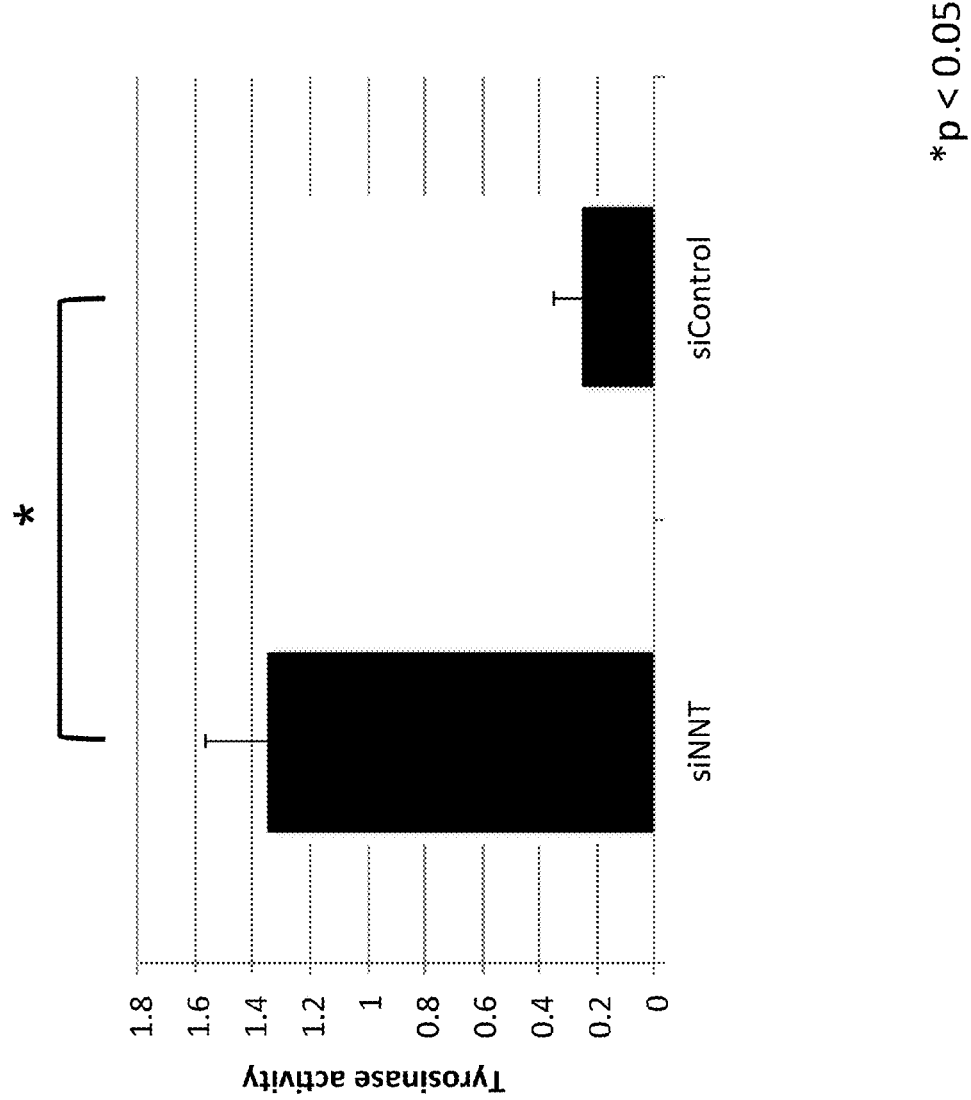
FIG. 17 Mushroom tyrosinase activity assay in UACC257 cells: Silencing of NNT increases tyrosinase activity as compared to control. *, indicates significant differences ($p<0.05$).
Figure 18:
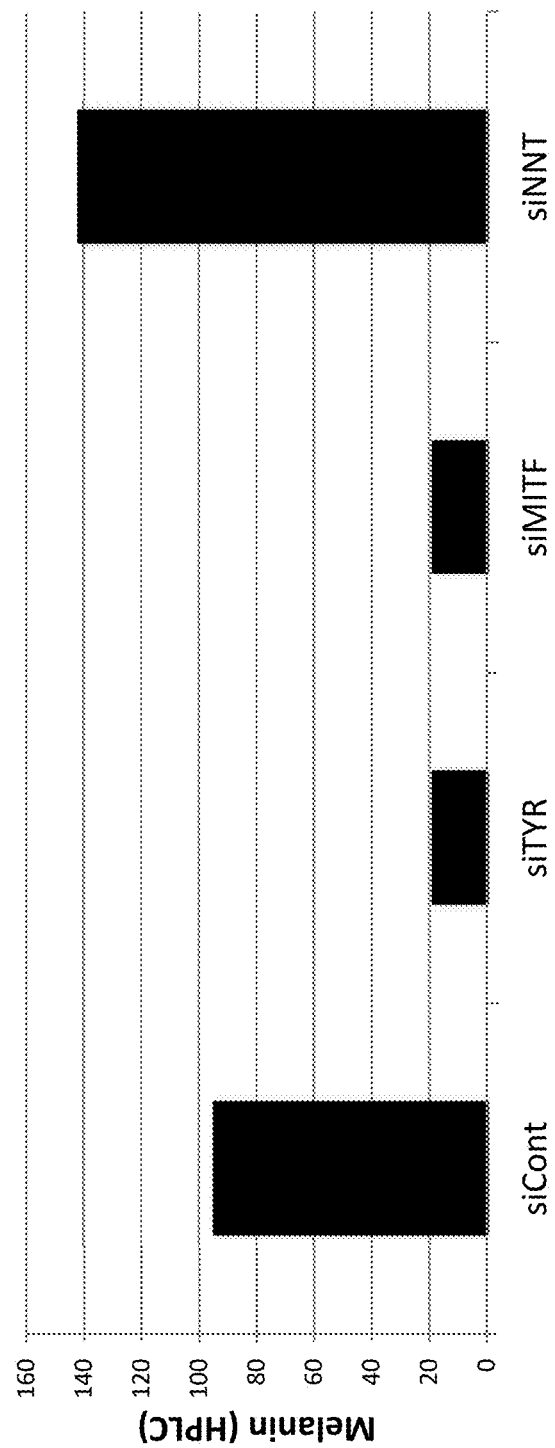
FIG. 18 Eumelanin measurements (method described in e.g., Ito et al., *Pigment Cell and Melanoma Research* 24(4): 605-613 (2011)) in UACC257 cells showed an increase of eumelanin after silencing of siNNT, and a decrease of eumelanin after treatment with siTYR and siMITF.
Figure 19:
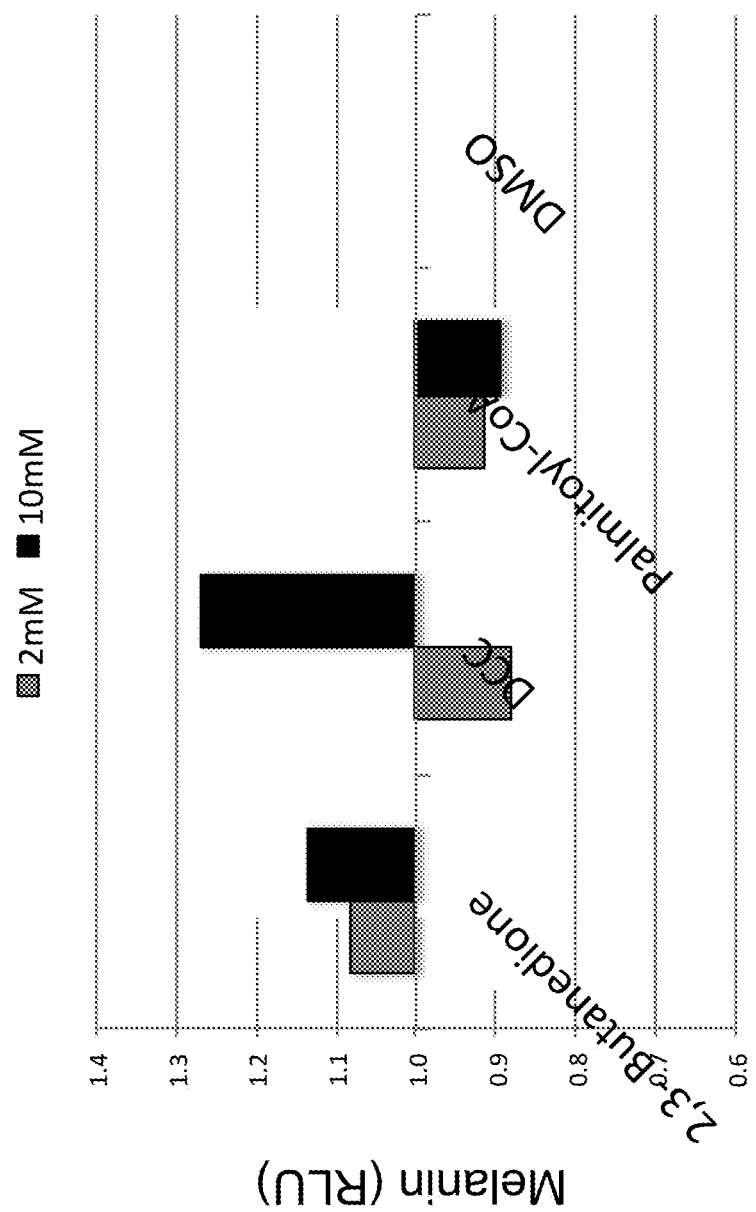
FIG. 19 Measurement of eumelanin in murine melanocytes (Melan-A cells) showed increased pigmentation after application of 2 and 10 mM 2,3-Butanedione and 10 mM of DCC indicating the impact of these NNT inhibitors on pigmentation.
Figure 20B:
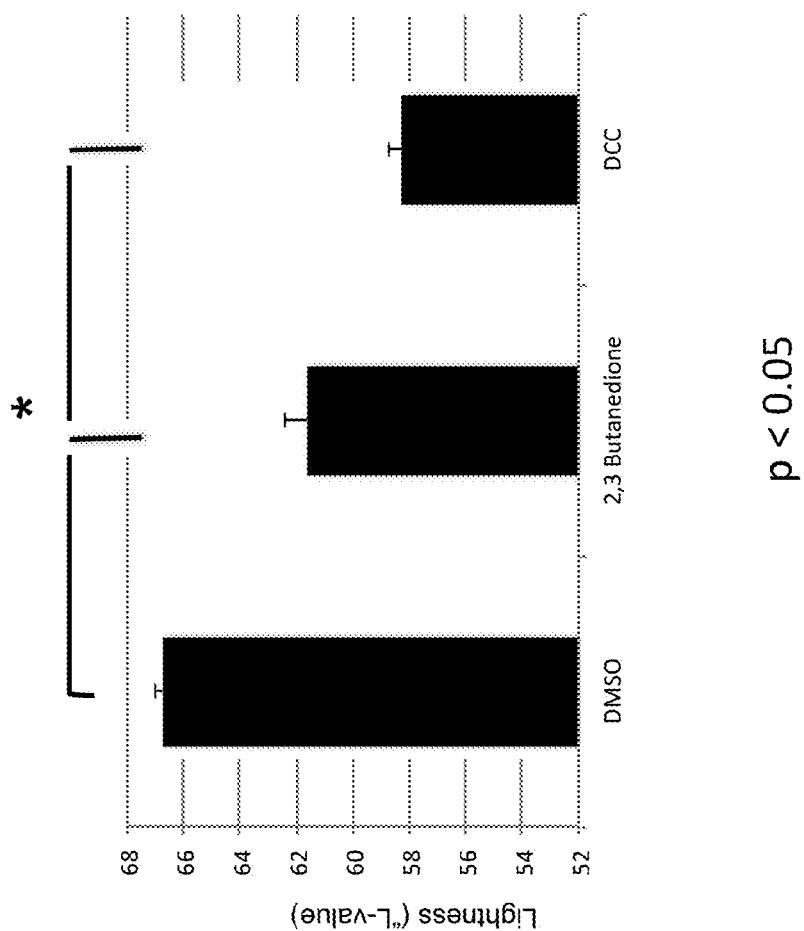
FIGS. 20A-20B show an increase in human skin pigmentation with treatment with an NNT inhibitor.
Figure 20A:
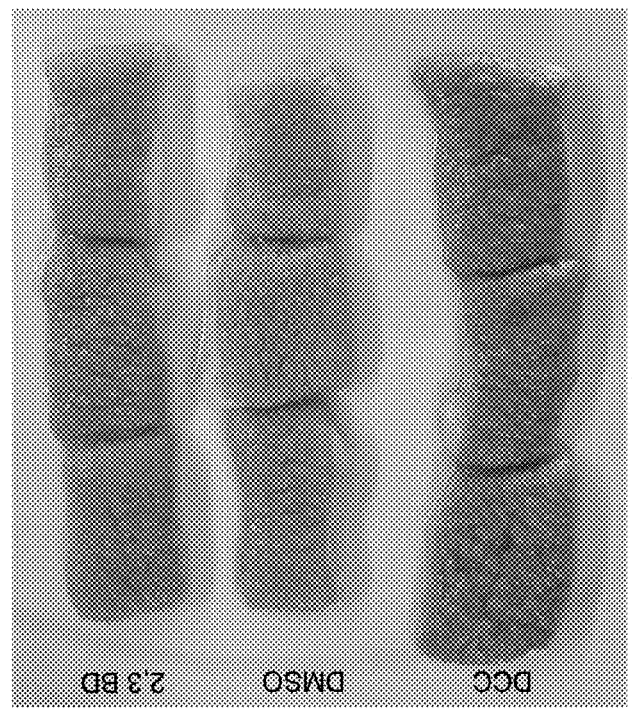

20B, Quantification of the pigmentation in FIG. 20A. The graph displays the decrease of lightness (~increase in pigmentation) measured via a colorimeter. *, indicates significant differences (p<0.05).

FIGS. 21A-21B Application of 50 mM 2,3 BD for 5 consecutive days once per day induces significant microscopic pigmentation as assessed using Fontana-Masson staining of skin samples (FIG. 21A). FIG. 21B, No significant inflammation or skin damage was observed in H&E stained skin samples.

Figure 22A:
Figure 22B:
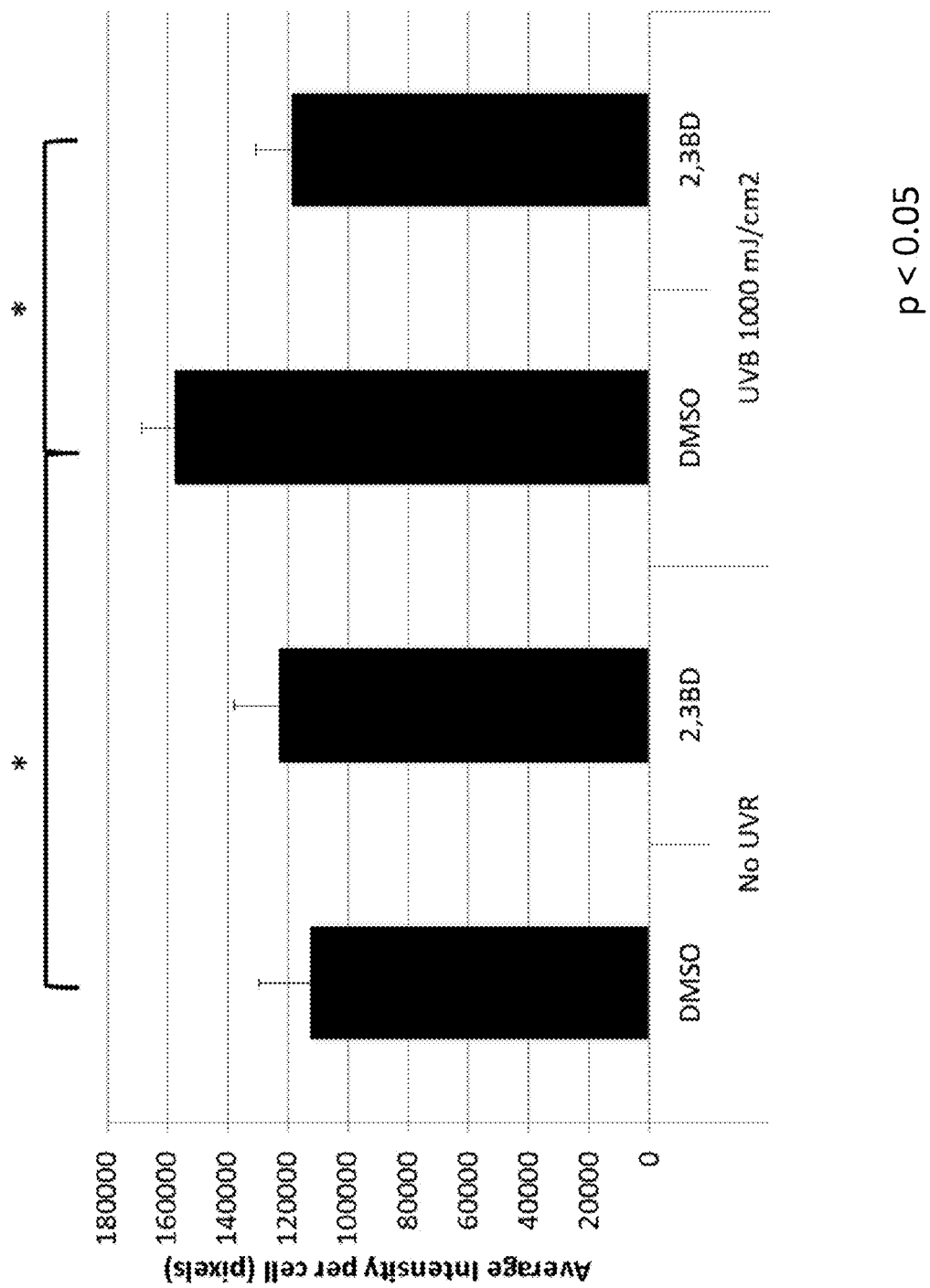

FIGS. 22A-22B shows CPD staining of human skin treated with 50 mM 2,3BD for 5 consecutive days (treatment once per day). On the last day skin was irradiated with 1000 mJ/cm$^2$ UVB showing a protective role for 2,3BD from UVB-induced CPD damage (CPD=cyclobutane dimer formation, a DNA damage, well known to cause carcinogenesis and melanoma development. 1000 mJ/cm2~3 h in the sun in India at noon (Balasaraswathy et al., India J Dermatol Venerol Leprol., 2002)).

FIG. 22A, are representative confocal images showing CPD staining. FIG. 22B, Quantification of the intensity of staining shown in the confocal images of FIG. 22A. *, indicates significant differences (p<0.05).

Figure 23:
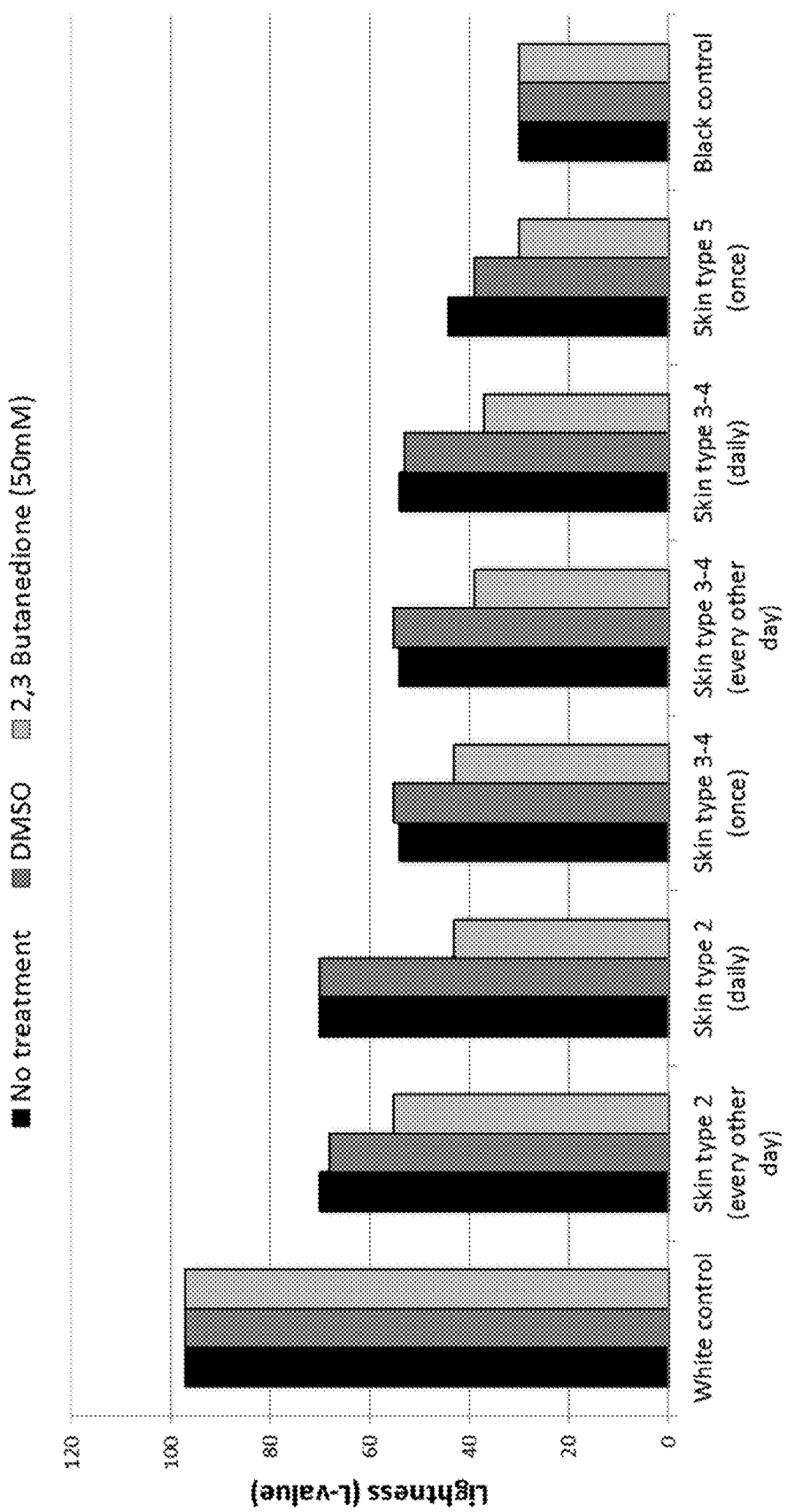

FIG. 23 Colorimetric measurements of eumelanin expression in different Fitzpatrick skin types. Skin patches were treated for 5 days.

Figure 24:
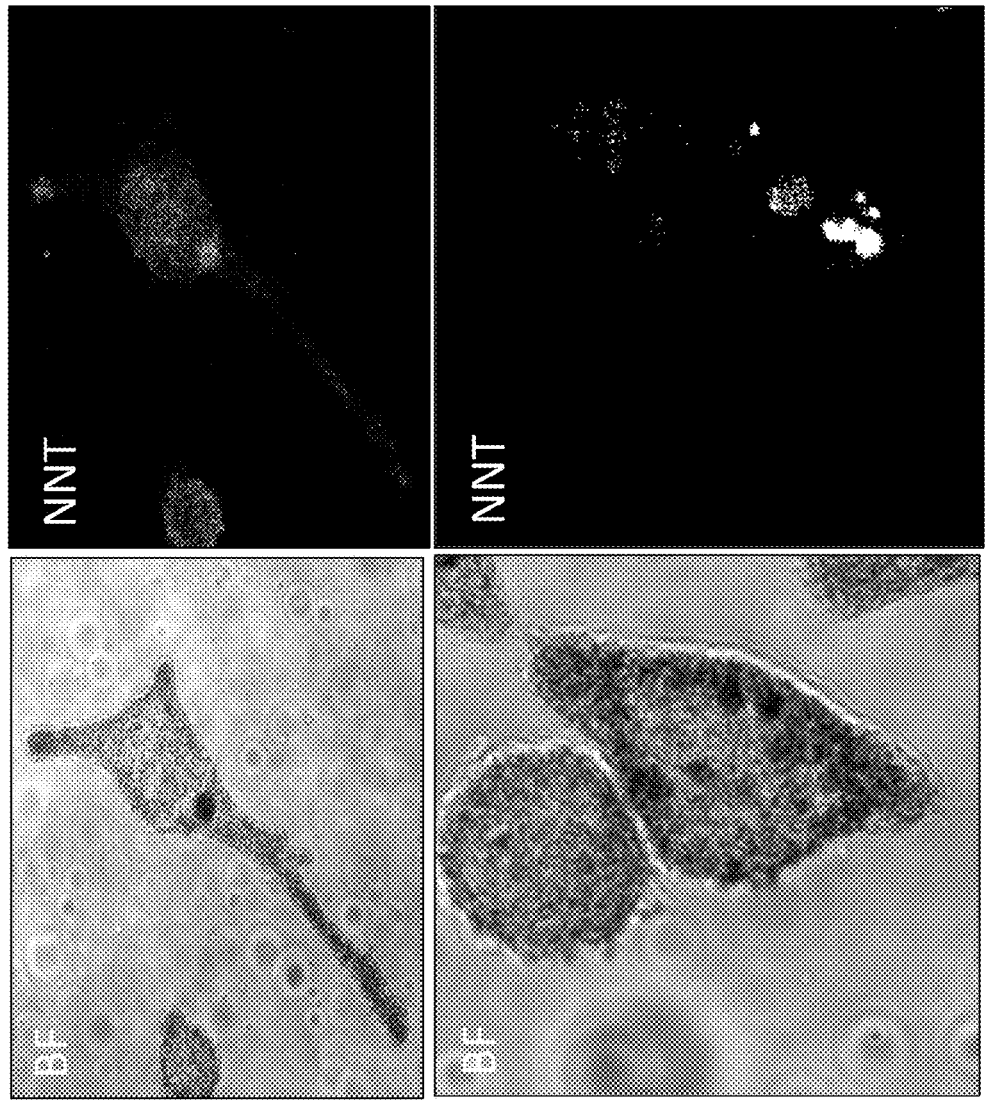

FIG. 24 Confocal imaging using antibodies targeting NNT. Imaging of human primary melanocytes (WM26) and human melanoma cells (UACC257) showed co-localization of NNT and melanosomal structures around the nucleus and distal cellular areas. Images were converted to black and white.

Figure 25A:
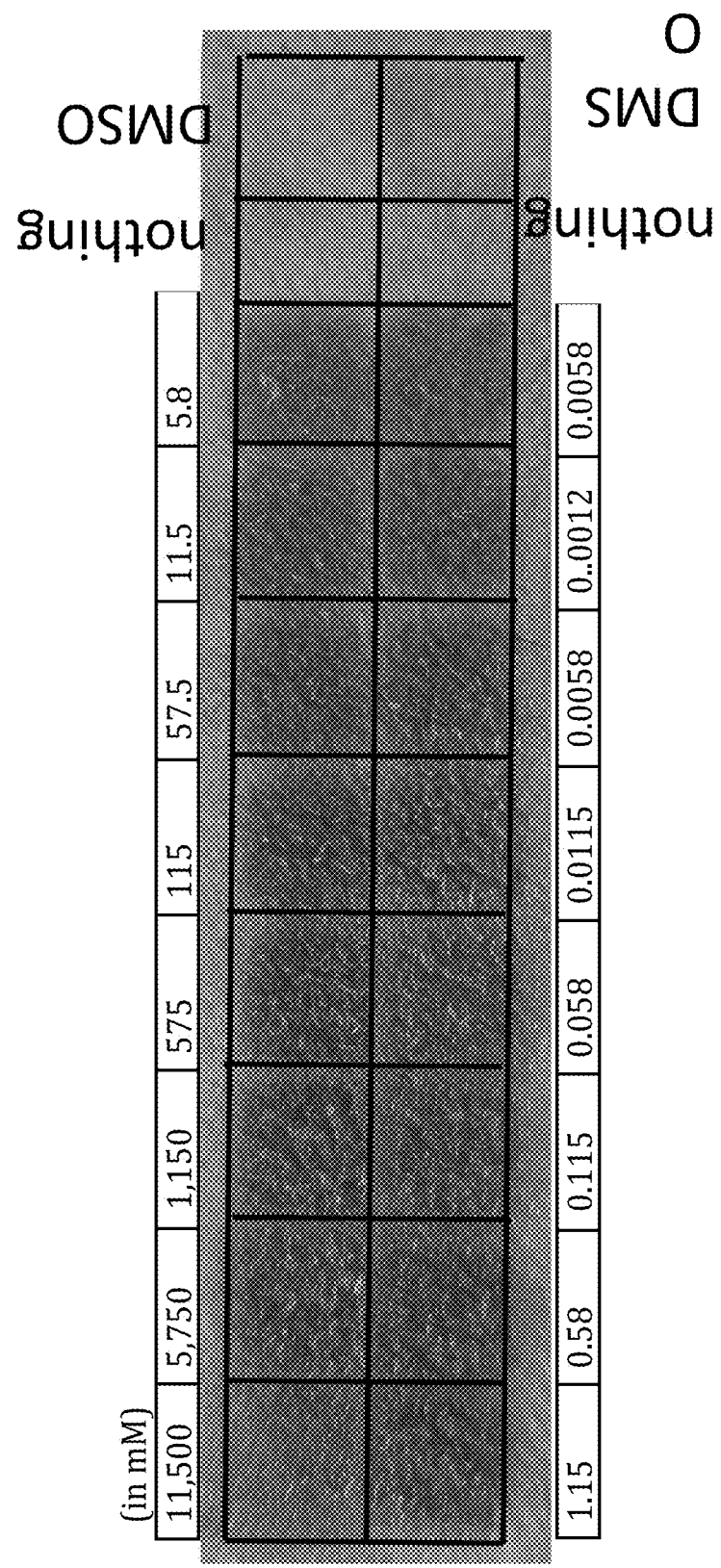
Figure 25B:
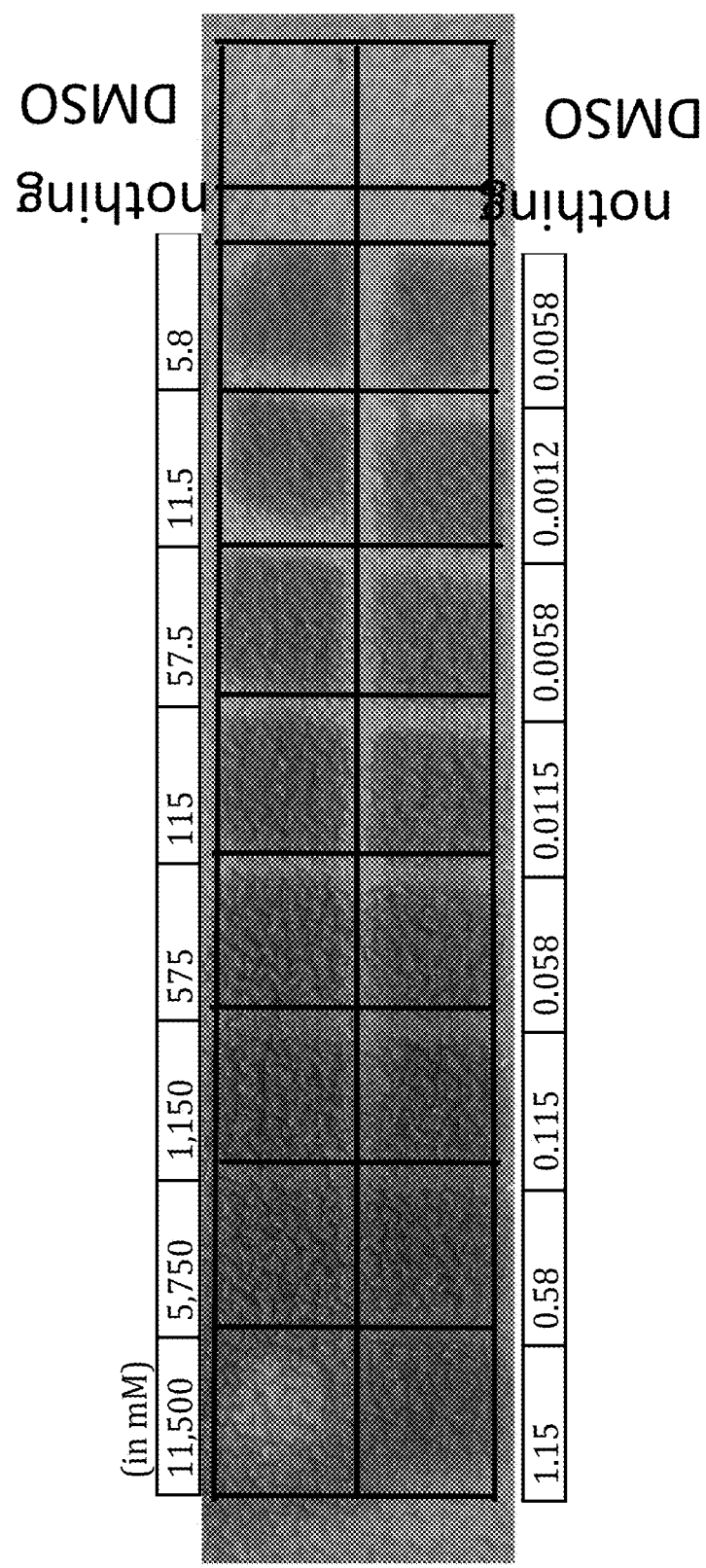
Figure 25C:
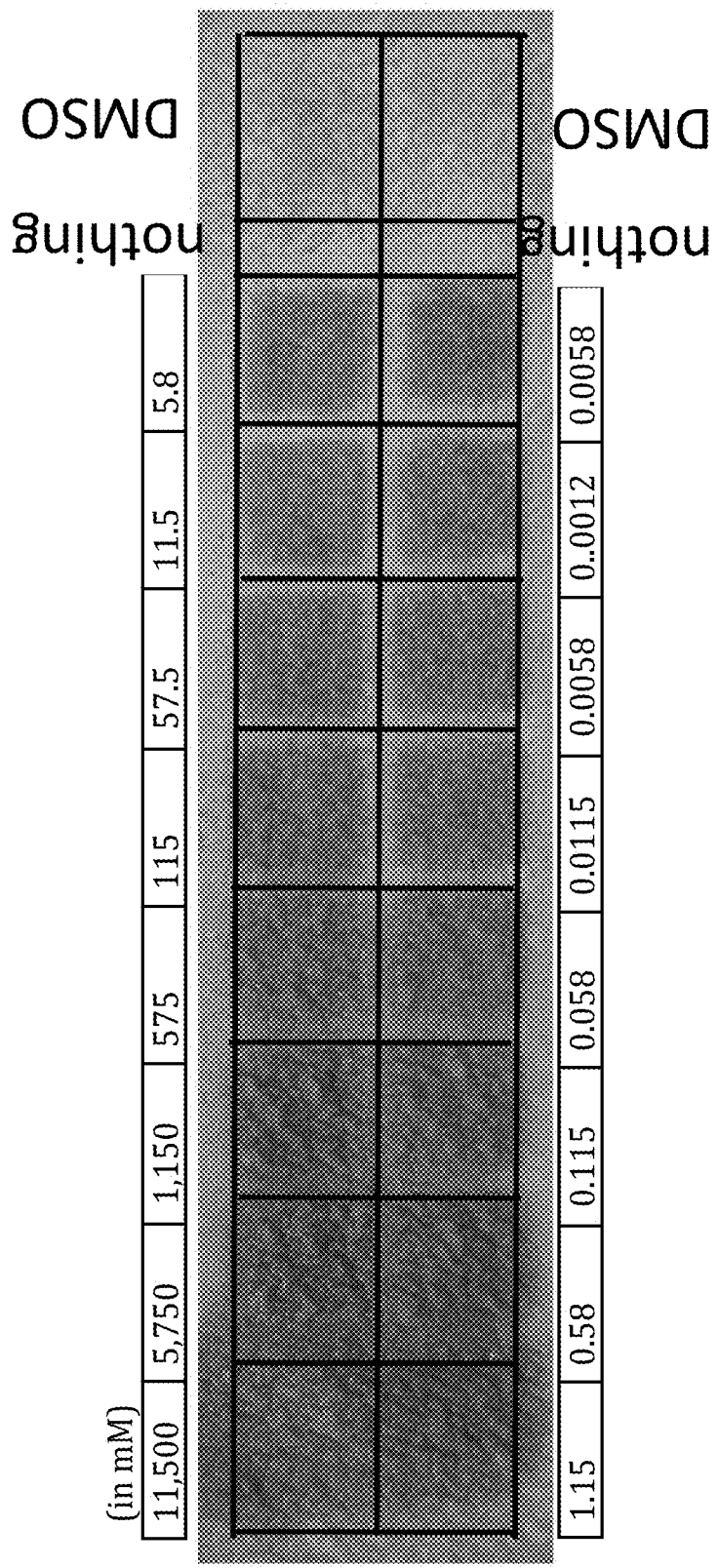

FIGS. 25A-25C Dose titration of 2,3 Butanedione (mM) (carrier=DMSO). FIG. 25A, Human skin explant from intermediately pigmented donor (Fitzpatrick skin type 3-4). Control on right side, treatment in decreasing concentration on left side. Treatment once per day for 5 consecutive days. FIG. 25B, Human skin explant from intermediately pigmented donor (Fitzpatrick skin type 3-4); Control on right side, treatment in decreasing concentration on left side. Treatment on day 1 and day 3. FIG. 25C, Human skin explant from intermediately pigmented donor (Fitzpatrick skin type 3-4). Control on right side, treatment in decreasing concentration on left side. Treatment once per on day 1, then wait for 5 days. Note: A one-time application of very low 2,3BD dosages might be enough for this donor to increase the individual's skin type of 2-3 classes (e.g. skin type 5-6)

Figure 26A:
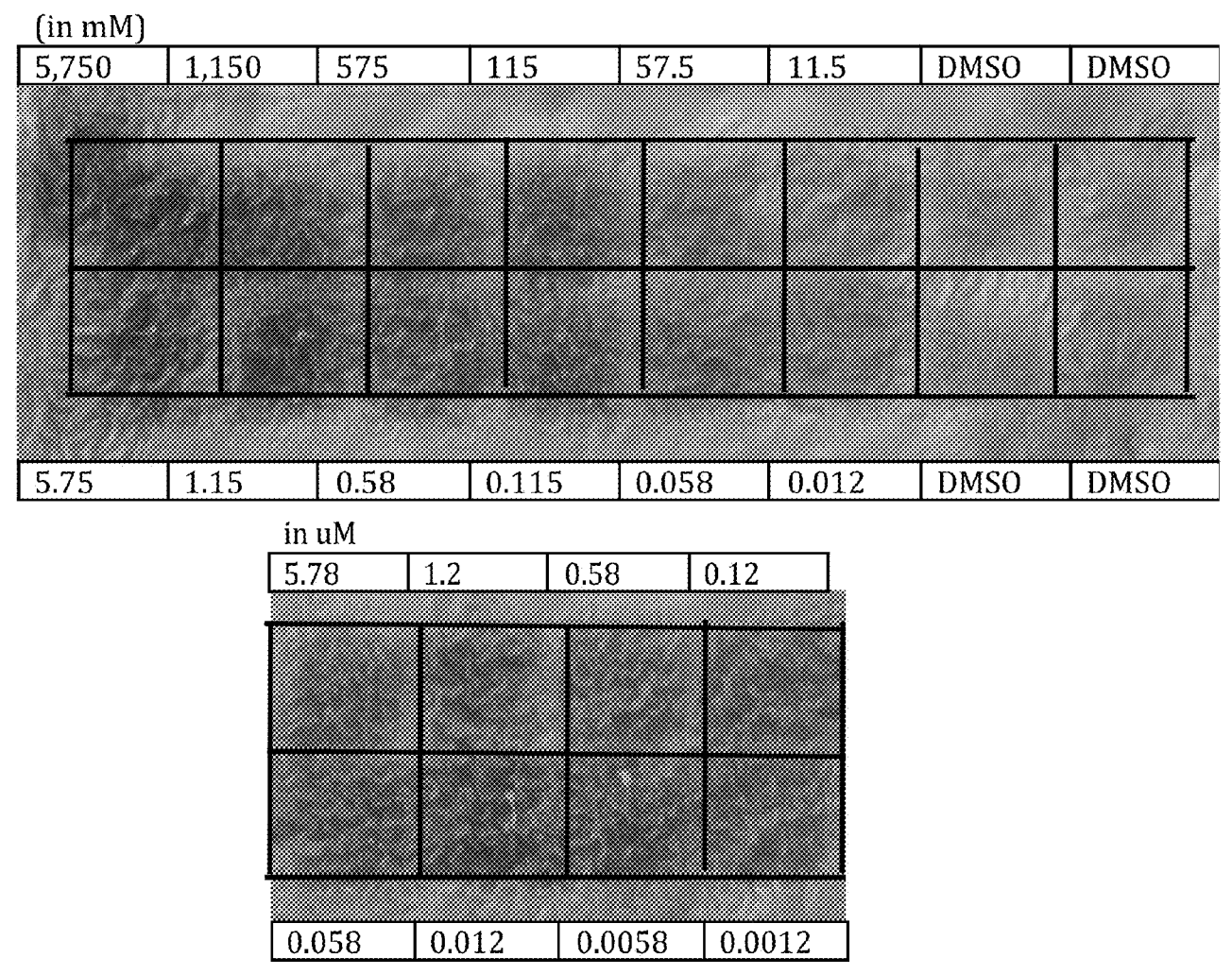
Figure 26B:
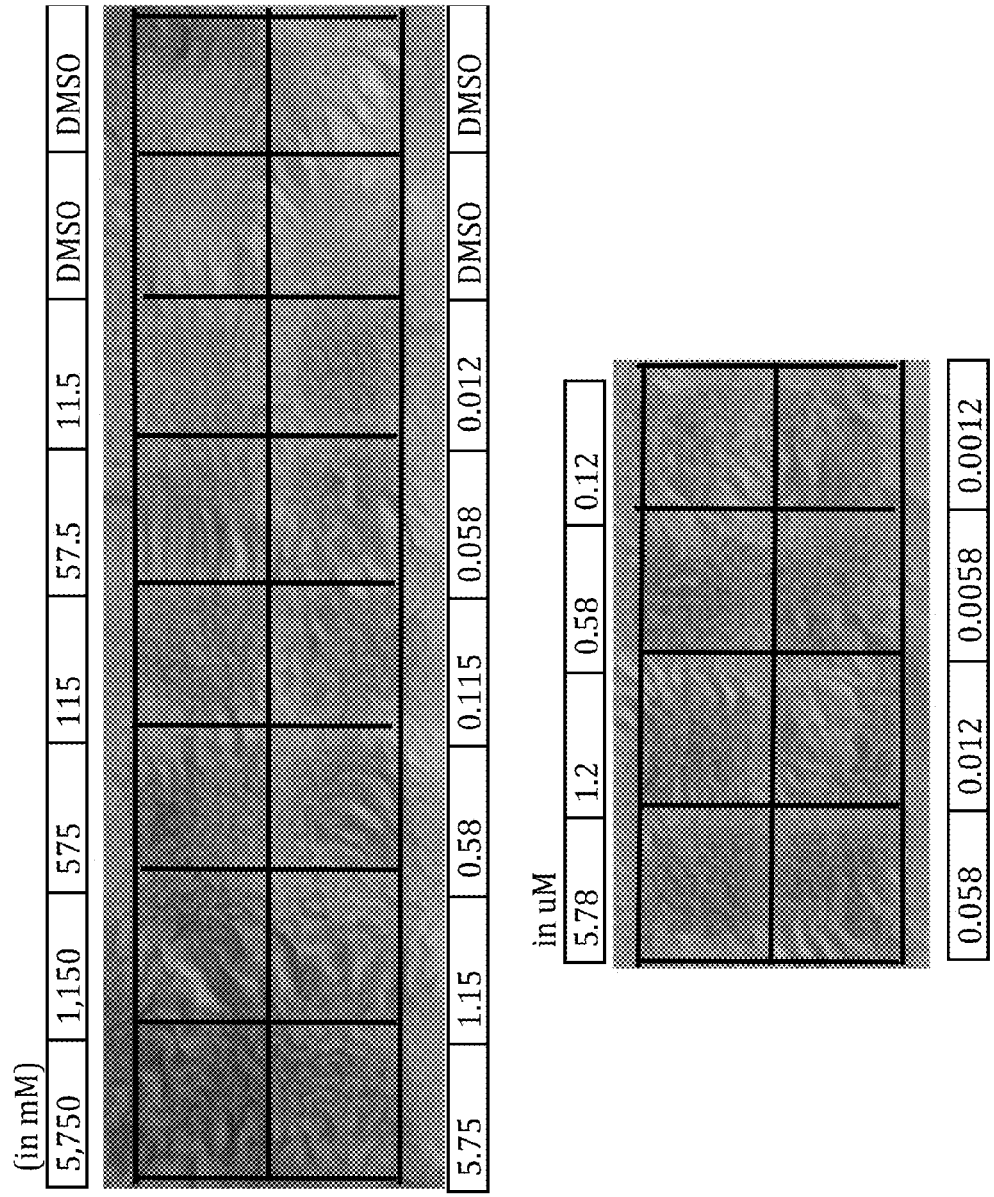

FIG. 26A-26B Skin type 2 (Fitzpatrick Scale): Increasing concentrations of 2,3BD (in DMSO) increase pigmentation. FIG. 26A, Human skin explant from a lightly pigmented donor (Fitzpatrick skin type 2); Daily treatment for 5 consecutive days. Note: The lower the Fitzpatrick skin type is (e.g. skin type 2) the more skin tends to become red and the harder it is to induce pigmentation (similar to an individual's natural tanning ability). One of skill in the art will appreciate that treatment strategies (dose and time) are adjusted based on the needs of the individual. FIG. 26B, Human skin explant from a lightly pigmented donor (Fitzpatrick skin type 2); Treatment on day 1 and 3. Wait for total 5 days until readout of pigmentation. Note: Very low dose treatment applied infrequently, e.g. every other day can be a suitable treatment strategy for this skin type to switch to a skin type 3-4 with significantly lower melanoma risk and without achieving any redness.

Figure 27:
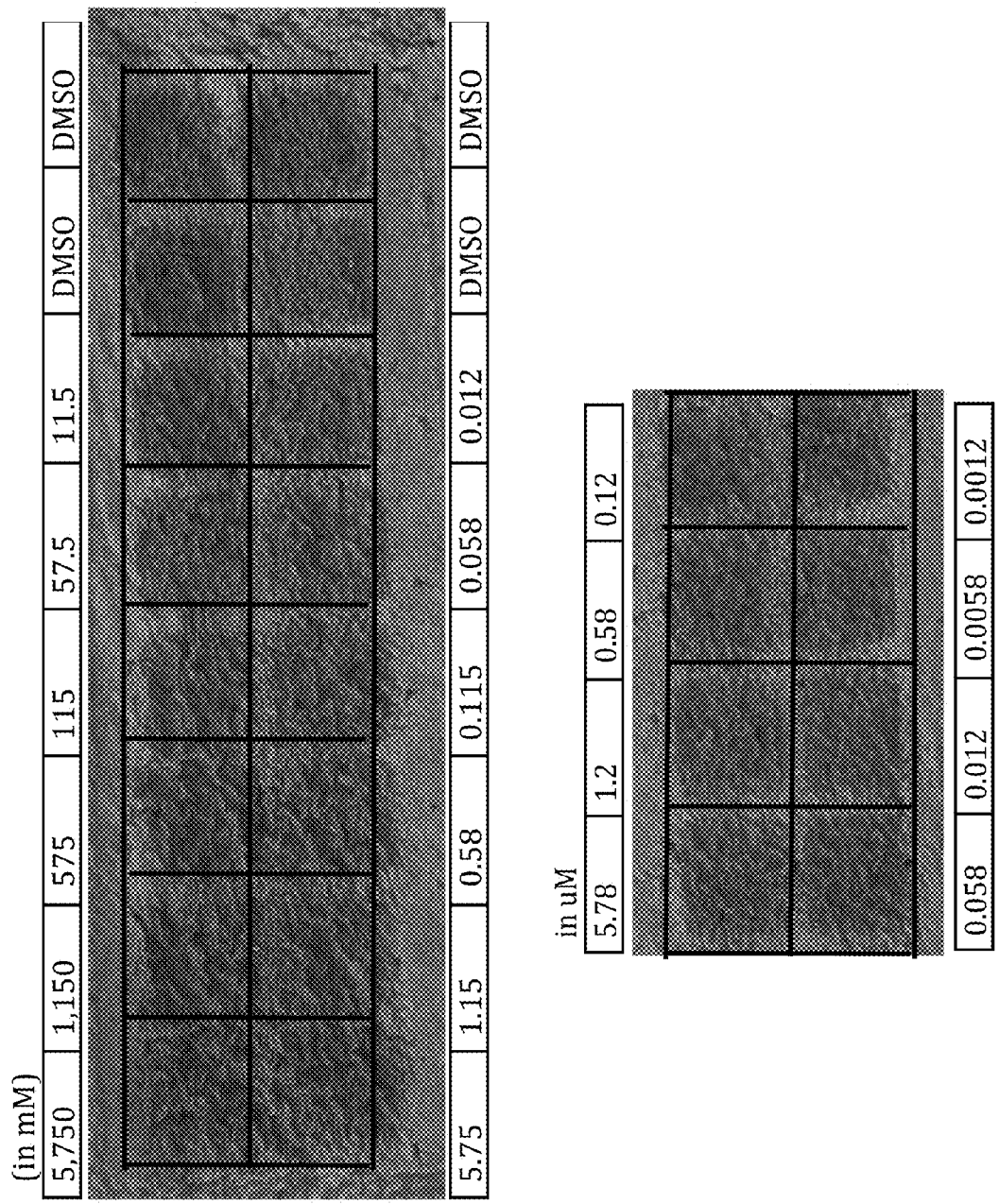

FIG. 27 Human skin explant from a deeply pigmented donor (Fitzpatrick skin type 5). Dose titration of 2,3 Butanedione (mM) in DMSO. One treatment on day 1. Then wait for total 5 days until readout of pigmentation. Note: Dark skin pigments very easy (even the carrier induces pigmentation), requiring an extremely low dose of 2,3BD applied only once in a different formulation to induce the maximal in humans achievable pigmentation (skin type 6). For further comparison please see quantification in FIG. 22.

Figure 28B:
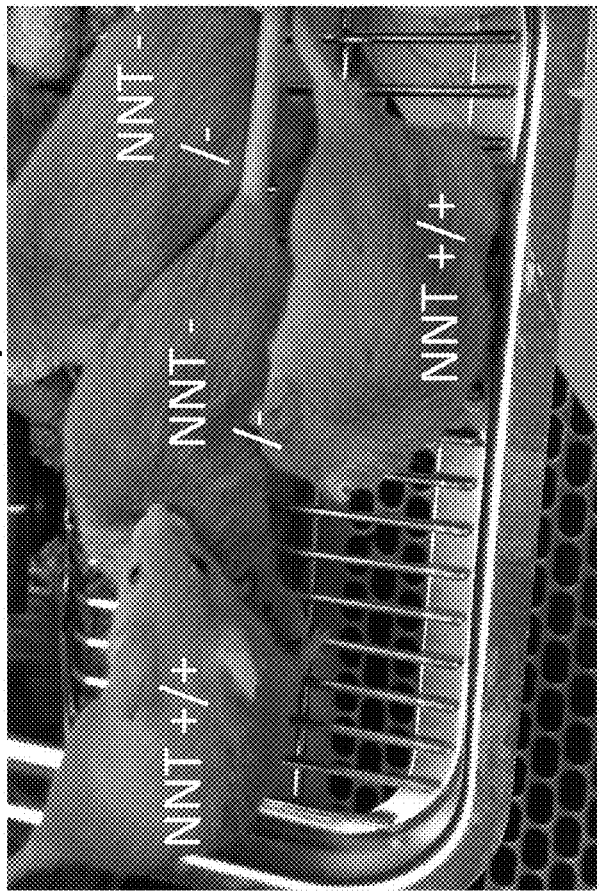
Figure 28A:
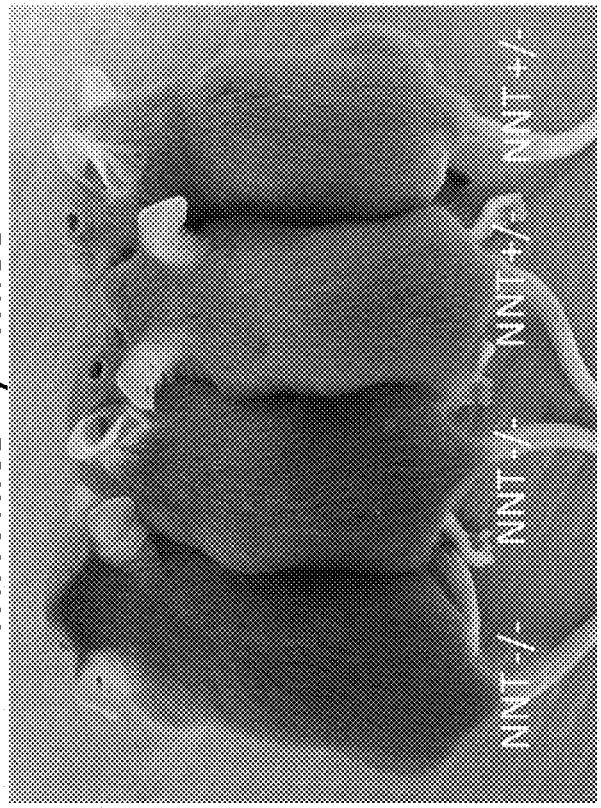

FIGS. 28A-28B, Fur pigmentation was observed in mice of different strains: grey MiWithe+/− (FIG. 28A), and red Mc1R e/e (FIG. 28B) mice showing a difference in their fur pigmentation according to their NNT status.

Figure 29:
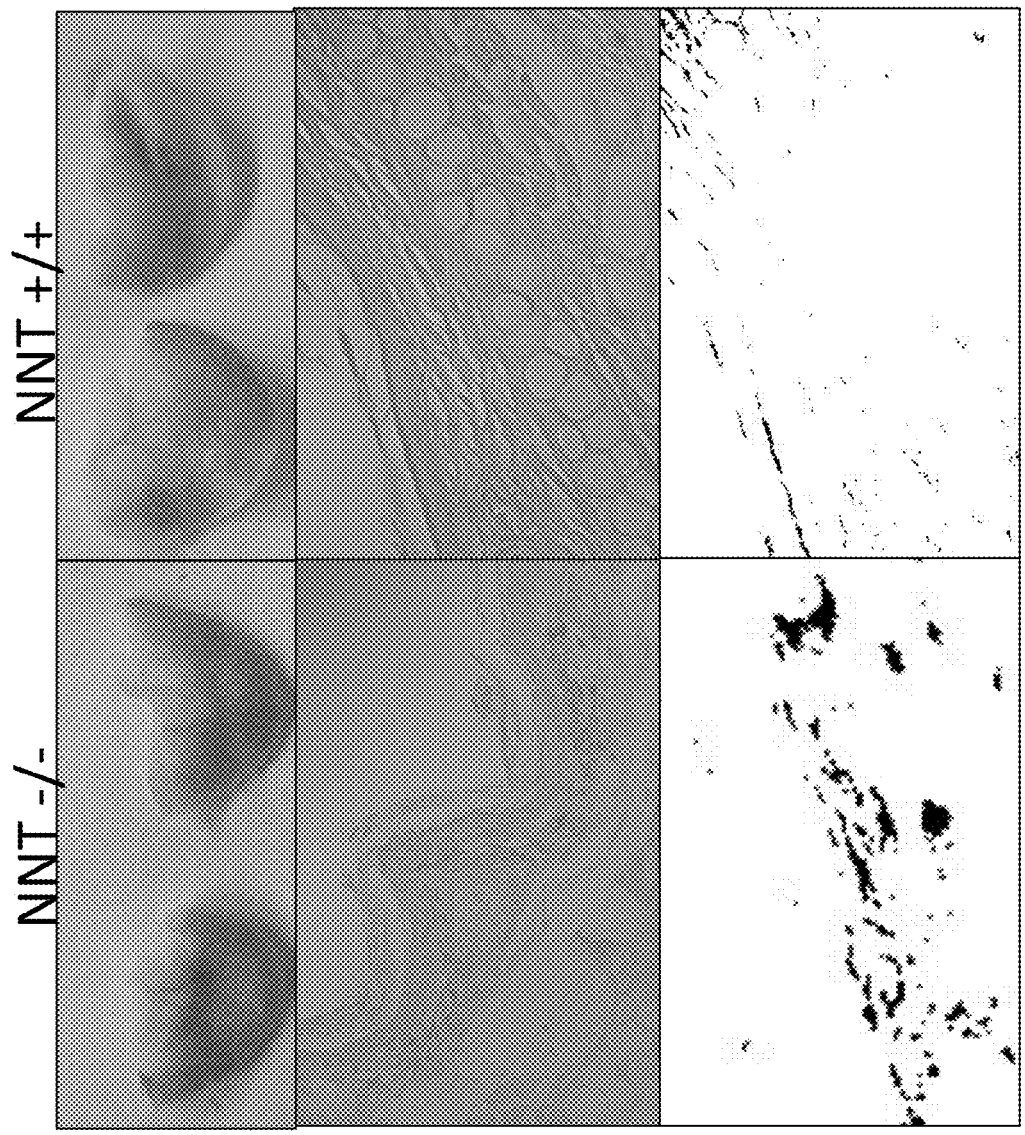

FIG. 29 Ears of MiWhite+/− (NNT+/+ vs. NNT−/−) were investigated via H&E staining Increased pigment formation was observed macro- and microscopically. Upper panel: Macroscopic pictures. Middle panel: Microscopic pictures. Lower panel: Melanin displayed

DETAILED DESCRIPTION

Provided herein are methods and compositions for enhancing hair and/or skin pigmentation in a subject, such methods and compositions comprise administering a composition comprising an agent that modifies the redox status of e.g., a melanocyte. In one embodiment, the agent that modifies the redox status of a melanocyte is an inhibitor of nicotinamide nucleotide transhydrogenase (NNT).

Definitions

As used herein, the term "enhancing hair and/or skin pigmentation," in its simplest form refers to the visual darkening of skin and/or hair following treatment of a subject or a hypopigmentation affected area as described herein of at least 10% as compared to a reference sample. In other embodiments, "enhancing hair and/or skin pigmentation" refers to a visual darkening of skin and/or hair of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level. In certain embodiments, the term "enhancing hair and/or skin pigmentation" can refer to an increased expression of eumelanin of at least 1% (e.g., at least 5%, at least 10%, at least 11%, at least 12%, at least 13%, at least 14%, at least 15%, at least 16%, at least 17%, at least 18%, at least 19%, at least 20%, at least 25%, at least 30%, at least 40%, at least 50%, at least 75%, at least 1-fold, at least 2-fold or more) in a biological sample obtained from a subject or affected area compared to a reference sample. It will be appreciated that very small changes in eumelanin expression can translate to very large changes in pigmentation, or skin darkening. Methods for quantifying enhanced hair and/or skin pigmentation include e.g., quantitative protein analysis of eumelanin as described herein.

As used herein, the terms "affected area," "affected region," "hypopigmentation area," and the like are used to refer to a patch or localized region in an individual having a hypopigmentation disorder. In certain embodiments, the patch or localized region may be surrounded by normal pigmented skin. In other embodiments, there can be a single affected area or multiple affected areas (e.g., 2, 3, 4, 5, 10, 15, 20, 50, 100 or more) in a single subject. The affected area can be of any size or shape provided that it is visible to the naked eye. It will be readily apparent to one of skill in the art that the methods and compositions provided herein are applied over the entire body of a subject to provide global protection. This global treatment can also be applied to those having an affected area (i.e., treatment is extended beyond the region of hypopigmentation).

As used herein, the term "biological sample" refers to a sample obtained from a subject that comprises at least one melanocyte. Such biological samples can include skin scrapings, a shave biopsy, a punch biopsy, an excisional biopsy, and the like.

As used herein, the terms "redox state," redox status," and "reduction/oxidation state/status" are used interchangeably to refer to the balance between the oxidized form and reduced form of proteins in a cell. For example, the redox state is represented by the reduced/oxidized ratios of proteins that are reversibly modified by reactive oxygen species (e.g., redox pairs). That is, the ratio of reduced groups (thiols) to oxidized groups (disulfide) is a measure of the redox status of proteins, cells or tissues. The redox ratios of such redox pairs can collectively provide a snapshot of the amount of oxidative stress that the cell is under at the time of measurement, and indicate the redox status of the cell or sample. The reversible reduction or oxidation of such proteins induces cell signaling mechanisms for e.g., modifying gene expression (e.g., eumelanin). Exemplary redox pairs useful for assessing the redox status of a cell or sample include NAD+/NADH, NADP+/NADPH, GSH/GSSG, among others.

As used herein the terms "reduce," "reduction," "decrease," or "inhibit" refer to a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "enhanced," "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "effective amount" as used herein refers to an amount sufficient to achieve a beneficial or desired cosmetic or clinical result upon treatment. Specifically, the term "effective amount" means an amount of a compound as described herein that is sufficient to increase hair, eye, and/or skin pigmentation in a subject, as that term is used herein.

The term "effective amount" can also refer to the amount of a therapeutic agent (e.g., an NNT inhibitor) that reduces at least one symptom of a disease or disorder to be treated (e.g., hypopigmentation, grey hair etc.), for example, by at least 10%. In addition, the term "effective amount" refers to an amount of an NNT inhibitor that can produce a desired degree of skin, eye or hair pigmentation for cosmetic purposes. Effective amounts will vary, as recognized by those skilled in the art, depending on the specific disease treated or the degree of cosmetic pigmentation desired, the route of administration, the excipient selected, and the possibility of combination therapy. Determination of an effective amount is well within the capability of those skilled in the art. Generally, an effective amount can vary with the potency of the agent used, the subject's history, age, condition, sex, Fitzpatrick skin type, as well as the severity and type of the medical condition in the subject or the degree of cosmetic pigmentation desired, and administration of other pharmaceutically active agents.

Physiological effects of a compound as disclosed herein on the subject can be measured to determine the effective amount include, without limitation, levels of reactive oxygen species, NAD+/NADH ratios, GSH/GSSG ratios, visual inspection of an affected area of hypopigmentation, improved confidence of the subject to be treated, reduced wrinkling, reduced skin aging, reduced formation of age spots, reduction in need for hospitalizations or medical interventions etc. In one embodiment, the physiological effect of a therapeutic compound is monitored by detecting and/or quantifying the amount of reactive oxygen species in a biological sample or the redox status thereof, using e.g. the methods and assays described herein.

The term "biological sample" as used herein refers to a sample that comprises a biomolecule and/or is derived from a subject. Representative biomolecules include, but are not limited to total DNA, RNA, miRNA, mRNA, and polypeptides. The biological sample can be used for the detection of the presence and/or expression level of eumelanin, reactive oxygen species, pheomelanin, GSH, GSSG, NADH, NAD+, etc. In some embodiments, the biological sample is a relatively readily obtained biological sample, such as for example, blood or a component thereof, or a tissue biopsy. Typically, the biological sample is obtained from an area of skin or hair from a subject to be treated with an NNT inhibitor as a pigmentation agent (e.g., tissue scraping, tissue biopsy, tissue punch, fine needle biopsy etc.). However, the biological sample can also comprise milk, blood, serum, plasma, ascites, cyst fluid, pleural fluid, peritoneal fluid, cerebral spinal fluid, tears, urine, saliva, sputum, or combinations thereof. In some embodiments, the sample includes a cell culture sample.

The term "melanoma" refers to a tumor or lesion arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Reactive Oxygen Species and Skin Pigmentation

Data from the United States Surveillance, Epidemiology, and End Results (SEER) registry showed that malignant melanoma was the most rapidly increasing malignancy in both sexes in the USA during 1973-1997. In the US over 76,000 new cases and about 10,000 deaths are registered per year, resulting in a lifetime risk of currently around 1/50. Since 1973 the age-adjusted melanoma incidence rates almost tripled among males, from 6.7 in 1973 to 19.3 in 1997, and more than doubled among females, from 5.9 to 13.8 (Jemal et al., 2001). Even though it has been hypothesized that this effect is due to an improved melanoma screening system, Mitra et al. showed that oxidative stress is a major risk factor for the development of melanoma. So far, it is known that, in humans, the naturally occurring dark pigment eumelanin is a very potent ROS-scavenger (Toda et al., 2010), and its counterpart, Pheomelanin, (which naturally occurs in higher levels in red-haired/fair-skinned people) has been shown to increase ROS and induce melanoma formation in an UV-independent context (Mitra et al. 2012). Taken together these data indicate that an increase of eumelanin in human skin can be an excellent strategy to sufficiently protect human individuals from melanoma formation and hereby act as a sun blocking/ROS-absorbing agent.

Redox State

The term reactive oxygen species (ROS) is a generalized description for a collection of reactive oxygen molecules of biological significance. These include: superoxide ($O_2$), hydroxyl radical (OH.), peroxyl radical (ROO), alkoxyl radical (RO), hydroperoxyl radical (HOO), hypochlorous acid (HOCl), hydrogen peroxide ($H_2O_2$), ozone ($O_3$), singlet oxygen ($1O_2$) and peroxinitrite (ONOO).

ROS are often thought of as being directly detrimental to cell viability because they can irreversibly damage key macromolecules such as proteins, nucleic acids and lipids. However, reactive oxygen species can regulate signal transduction pathways linked to the control of cell proliferation, cell growth, gene expression, and cell death.

ROS, particularly those with mild oxidant capabilities, form suitable signaling molecules as they are capable of oxidizing the reduced thiol groups of cysteine residues to form disulfide bonds with glutathione, an adjacent cysteine residue or a small protein such as thioredoxin. This mild and reversible oxidation is referred to as thiol group modification. As ROS levels increase, more thiol groups become oxidized to disulfides. Consequently, the ratio of reduced groups (thiols) to oxidized groups (disulfide) is a measure of the redox status of proteins, cells or tissues.

Once oxidized, thiol group modifications can be reversed or reduced by specialized enzyme systems, such as thioredoxin or glutaredoxin. This reversible modification of a protein's cysteines between an oxidized and reduced state is analogous to the regulation of a protein's function by phosphorylation/dephosphorylation. Changes in the redox status of a protein, involving disulfide formation and glutathionylation, have been shown to affect the activity of several different signaling transduction proteins and it is thought that changes in the thiol redox status may influence many aspects of cell function, viability and survival.

Mammalian tissues are rich in protein thiols (20-40 mM) and many intracellular proteins have been identified that can undergo thiol group modification.

One essential aspect of cellular energy metabolism is the reduction-oxidation (redox) state of the cell. During cellular energy metabolism, energy is often stored and released as part of redox reactions. Major co-factors in these metabolic reactions are the nucleotides NAD(P) and NAD(P)H. The redox state of a cell is described as the balance between the oxidized form of these nucleotides (NAD(P)) and the reduced form (NAD(P)H). The redox state is studied in order to determine the metabolic status of live cells and can be used to study enzymes and metabolites that are involved in the redox state and/or utilized directly or indirectly the NAD(P)/NAD(P)H nucleotides. Methods currently exist to study the redox state of cells, including tetrazolium salts (MTT, MTS, and XTT) and resazurin. All of these methods involve compounds that are reduced in metabolically active cells to produce either a colorimetric or fluorescent signal.

The molecules NAD and NADP, and their reduced forms NADH and NADPH, are cofactors present in all organisms. They are involved in many and multiple oxidoreductase reactions critical to cell metabolism as well as function in other necessary cellular processes. Often, it is desirable to measure the levels of NAD, NADP, NADH, NADPH as an indication of cellular redox state and its perturbation by treatments.

The redox status of a cell or tissue can also be assessed by measuring analytes that can be detected by coupling to NAD(P)H production or by measuring major metabolites that reflect redox state balance of the cells, e.g., lactate, pyruvate, beta-hydroxybutyrate, acetoacetate.

Melanin

The coloration of human skin is determined by the concentration of melanin produced by the melanocytes. The melanocytes are specialized cells, which synthesize melanin by means of specific organelles, the melanosomes. The same holds true for the coloration of eyes, hair on the head and body, as well as the fingernails and toenails.

A reservoir of melanocytes exists in hair follicles. When the hair follicular melanocytes are activated, hair and skin have enhanced pigmentation. Thus a greater number of melanocytes present in the hair follicles lead to greater pigmentation in the skin and hair. Hypopigmentation of the skin and hair in humans and animals results from local defects in the melanin production within the melanocyte.

Synthesis of melanin within a melanocyte is controlled by the activity of an enzyme, tyrosinase, which is localized in an intracellular organelle—the premelanosome. Upon activation of tyrosinase, melanin is deposited with the organelle. After complete melanization, the premelanosome is known as a melanosome. Melanosomes are delivered to surrounding keratinocytes of the skin cells within the shaft of the graying hair by the process known as cytocrine secretion. Melanin synthesis occurs within the melanosomes in the presence of the oxidative enzyme tyrosinase, which converts tyrosine to dihydroxyphenylalaline (DOPA) and subsequently to DOPAquinone.

Enhancing Skin, Eye and/or Hair Pigmentation

In Individuals lacking a hypopigmentation disorder: Darker skin pigmentation is considered desirable by many persons, socially and aesthetically. At present, the most common means of darkening skin is sun-tanning, using either natural sunlight or specially designed ultraviolet light sources (tanning lamps). However, extended exposure of human skin to ultraviolet light is well known to have adverse long and short term health consequences, specifically skin cancer and photoaging (long term) and the risk of painful sunburn and keratitis (short term). Furthermore, light-skinned individuals are highly susceptible to sun-induced skin cancers, face a higher risk of melanoma (skin cancer), and incur photoaging or dermatoheliosis, a condition characterized by wrinkling, irregular pigmentation, and surface roughness. Thus, in one embodiment, the methods described herein can be used for cosmetic purposes to enhance skin and/or hair pigmentation in an individual who is not necessarily affected by a hypopigmentation disorder.

Sunless Tanning: A sun tan is the consequence of the enhanced production of the pigment melanin in the epidermis, in response to exposure of the skin to ultra violet radiation, in a process referred to as melanogenesis. Tyrosine is converted, in a series of steps which are under enzymatic control, to melanin, a key enzyme being tyrosinase, a metallo-enzyme dependent upon copper. (G. Prota, Recent Advances in the Chemistry of Melanogenesis in Mammals, J. Invest. Dermatol. 75(1), 122-7, 1980).

"Sunless tanning", also called self-tanning, is the ability to impart a tan to skin without the use of sunlight. In order to achieve a tanned look or otherwise darken their skin, individuals can expose their skin to sunlight or a source of simulated sunlight, e.g., a solar simulator or ultraviolet lamps. For many individuals, such exposure will stimulate formation of new melanin pigment and the retention of increased amount of melanin in the epidermis and produce a darkened skin color. However, some individuals find that such exposure does not produce the desired melanin formation and as a result the desired tan is not obtained. It is also well known that in lightly pigmented human skin, the ability to produce melanin through ultraviolet light is weak due to their genetic background involving polymorphisms in melanocortin 1 receptor (Mc1R) and expression of various pigmentation genes, such as MITF, Tyr, DCT, and TYRP1. Additionally, exposure to the sun or a source of ultraviolet radiation can have deleterious effects for many individuals and can, in fact, cause sunburn, skin blistering, premature skin aging or skin cancer. Self-tanning or sunless tanning compositions offer a safe alternative and enable these individuals to obtain the desired tanned look. Typical sunless tanning preparations sold to the consumer are in the form of a cream, lotion, gel or aerosol foam or spray. Additionally, within the last few years, indoor tanning salons have begun to offer automated sunless tanning spray applications as a safer alternative to UV tanning beds. These sunless tanning sprays are applied either in an enclosed booth or with a hand-held spray apparatus and involve the pressurized application of a sunless tanning solution containing DHA or combinations of DHA and erythrulose and are typically delivered over the entire body in the form of a mist.

Sunless tanning booth operations are described in U.S. Pat. No. 6,387,081; "Misting apparatus for application of coating materials to skin surface". Other US patents by Laughlin (U.S. Pat. Nos. 5,922,333; 6,199,557; 6,446,635; 6,474,343; 6,439,243, 6,431,180; and 6,305,384) by Parker (U.S. Pat. Nos. 6,443,164 and 6,302,122) and others describe automated spray systems for coating human skin with various cosmetic compositions including self-tanning compositions.

Provided herein are methods and compositions useful as an alternative to traditional sunless tanning creams or sprays that utilize DHA to "stain" the skin. It is contemplated herein that an agent that modifies the redox state of a melanocyte (e.g., an NNT inhibitor) is used to induce eumelanin production, thereby resulting in sunless tanning. It will be appreciated by one of skill in the art that different dosages of the agent can be used to achieve differing degrees of tanning in the subject. These dosages will vary depending on the degree of pigmentation of the individual prior to treatment according to the methods described herein.

Cosmetic compositions using the methods described herein are applied topically and can be presented in a wide variety of different forms suitable for such application, for instance, oils, creams, gels, aqueous or alcoholic lotions, aerosol sprays or any other cosmetic formulation conventionally used for sun tan products.

In addition, a cosmetic carrier can be added to the agents useful in the methods described herein. The major requirement of the carrier is that it is cosmetically acceptable and is compatible with the active ingredients of the composition i.e. the carrier does not inhibit the tan accelerator action. The carrier may itself have some efficacy as a tan accelerator, if so desired. Examples of suitable carriers include sodium stearate; glyceryl stearate and PEG-100 stearate; glyceryl-stearate/PEG-30 stearate; sorbitan monostearate, PEG-7 hydrogenated castor oil; beeswax and stearic acid/PEG-7 hydrogenated castor oil; methoxy PEG-22 dodecylgycol copolymer/PEG-45 dodecylglycolcopolymer/hydroxyoctacosanyl hydroxystearate; diethanolamine cetylphosphate/glycerylstearate; methylglucose sesquistearate/methylgluceth-20 sesquistearate; and polyglycol-2-PEG-4 stearate/diethanolamine cetylphosphate.

Other methods and considerations for use of the agents described herein as sunless tanners or cosmetic compositions are known to those of skill in the art and are not described in detail herein.

It will be appreciated by one of skill in the art that any enhancement of skin pigmentation, even for cosmetic purposes, can prevent further sun-associated skin damage and also protect the subject from a variety of skin cancers. For example, the methods and compositions provided herein can provide protection from general DNA damage, basal cell carcinoma, squamous cell carcinoma, melanoma, malignant melanoma, actinic keratosis, Kaposi's sarcoma, Bowen's disease, and merkel cell carcinoma. In other embodiments, the methods and compositions provided herein, in addition to enhancing skin, eye and hair pigmentation, can also provide protection from sun-induced damage and other cosmetic concerns including, for example, DNA damage, seborrheic keratosis, moles, wrinkles, liver or age spots, skin sagging, bags under the eyes, loss of skin elasticity, uneven skin tone, freckles, melasma (e.g., mask of pregnancy), actinic cheilitis, cataracts, etc.

Hair Coloring: Hair coloring is the practice of changing the color of hair. The main reasons for this practice are cosmetic (e.g., to cover gray hair, to change to a color regarded as more fashionable or desirable, or to restore the original hair color after it has been discolored by hairdressing processes or sun bleaching). Today, hair coloring is immensely popular, with over 75 percent of American women dyeing their hair and globally hair colorants are a rapidly growing over-$7 billion industry.

The compositions and methods described herein are contemplated for use in hair coloring. In certain embodiments, the hair coloring using the methods described herein can be permanent, semi-permanent, or temporary.

In one embodiment, the agents described herein are formulated as a shampoo. In other embodiments, the agents described herein are formulated as a cream, a suspension, a solution, or by any other topical means as described herein. The cosmetic formulations for hair coloring can be applied or used e.g., daily, weekly, biweekly, monthly, or quarterly to induce and/or maintain the desired hair coloration. As hair is in a constant state of growth, it will be appreciated that administration in this manner will need to be maintained to keep the entirety of the hair a uniform color. In addition, it will be noted that the color of the hair already in place will likely not change with administration of the agents as described herein. Thus, in one embodiment, the subject undergoes a hair-cut or has the hair shaved to remove grey or lightly-colored hair to facilitate the new growth of hair comprising eumelanin pigment.

In another embodiment, the agents as described herein can be formulated with or administered in conjunction with another hair coloring agent e.g., that temporarily colors the shaft of the hair as the new hair (colored by the agents described herein) grows in, thereby avoiding an unsightly line of color descending from the scalp.

Other methods and considerations for use of the agents described herein as hair colorants or cosmetic compositions are known to those of skill in the art and are not described in detail herein.

Eye Coloring: There are melanocytes in the middle layer of the eye (uvea) that contribute to eye color. In humans, the pigmentation of the iris varies from light brown to black, depending on the concentration of melanin in the iris pigment epithelium (located on the back of the iris), the melanin content within the iris stroma (located at the front of the iris), and the cellular density of the stroma. The methods and compositions described herein can be used to modify the ration of eumelanin to pheomelanin, effectively darkening the pigmentation of the eye. In one embodiment, modification of eye pigmentation can protect against sun-induced damage or diseases in a subject, for example, formation of cataracts.

In individuals having a hypopigmentation disorder: Some individuals are unable to achieve even normal pigmentation due to abnormal conditions such as vitiligo, piebaldism, albinism, and other hypopigmentation disorders, or as the result of certain inflammatory processes. The result of such abnormal conditions, in the extreme, is total depigmentation of both hair and skin. In less severe instances, some hypopigmentation disorders result in patchy white areas within the skin and hair. In another embodiment, the methods described herein can be used for cosmetic purposes to enhance skin and/or hair pigmentation in an individual having a hypopigmentation disorder.

It will be appreciated by those of ordinary skill in the art that the methods described herein can only be used in individuals having a hypopigmentation disorder that also have existing melanocytes. Some non-limiting examples of hypopigmentation with existing melanocytes include vitiligo (early stages), Nevus depigmentosus, post-inflammatory/infectious hypopigmentation, tinea versicolor, pityriasis alba, scleroderma, ito hypomelanosis (incontinentia pigmenti achromians), and tuberous sclerosis.

Melanoma and Other Skin Cancers

In some embodiments, the methods and compositions described herein can be used to treat and/or prevent melanoma. Melanoma is a cancerous growth that develops when unrepaired DNA damage to skin cells (most often caused by ultraviolet radiation from sunshine or tanning beds) triggers mutations that lead the skin cells to multiply rapidly and form malignant tumors. These tumors typically originate in the pigment-producing melanocytes in the basal layer of the epidermis. The majority of melanomas are black or brown, but they can also be skin-colored, pink, red, purple, blue or white. Melanoma is caused mainly by intense, occasional UV exposure (frequently leading to sunburn), especially in those who are genetically predisposed to the disease, such as individuals with light skin and hair.

The methods and compositions provided herein can also protect against and/or prevent general DNA damage, basal cell carcinoma, squamous cell carcinoma, melanoma, malignant melanoma, actinic keratosis, Kaposi's sarcoma, Bowen's disease, and merkel cell carcinoma.

NNT Inhibitors and Derivatives Thereof

Nicotinamide nucleotide transhydrogenase (NNT) is an integral protein of the inner mitochondrial membrane. The enzyme couples hydride transfer between NAD(H) and NADP(+) to proton translocation across the inner mitochondrial membrane. Under most physiological conditions, the enzyme uses energy from the mitochondrial proton gradient to produce high concentrations of NADPH. The resulting NADPH is used for biosynthesis and in free radical detoxification.

Essentially any inhibitor of NNT can be used with the methods described herein, provided that the inhibitor is not toxic to living cells or tissue. Some non-limiting site-specific NNT inhibitors include N,N-Dicyclohexylcarbodiimide (DCC), 2,3-butanedione, palmitoyl CoA, and analogs or derivatives thereof.

In addition, one of ordinary skill in the art can determine whether a compound acts as a site-specific NNT inhibitor using the methods described by e.g., Rydstrom et al. *Eur J. Biochem* (1972) 31:496-504. In one embodiment, NNT inhibitors can be identified through chemical screening of a compound library and measuring e.g., the reactive oxygen species prior to and following treatment with chemicals from a screening library. Such methods are well known in the art and are not described in detail herein.

In one embodiment of the methods described herein, the NNT inhibitor is a small molecule. As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Also contemplated herein are derivatives and analogs of NNT inhibitors, including analogs and derivatives of e.g., N,N-Dicyclohexylcarbodiimide (DCC), 2,3-butanedione, and palmitoyl CoA. When designing a derivative, one of skill in the art will appreciate that the derivative or analog should not induce major side effects or have substantial toxicity to the subject. The chemical, biochemical or small molecules used for treatment of skin and/or hair pigmentation herein can include one or more of the following structural modifications.

Exemplary Chemical Modifications: As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound.

Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl(alkyl)amine, and cyano. Additionally, the suitable indicated groups can include, e.g., —X, —R, —O—, —OR, —SR, —S—, —NR2, —NR3, =NR, —CX3, —CN, —OCN, —SCN, —N=C=O, —NCS, —NO, NO2, =N2, —N3, NC(=O)R, —C(=O)R, —C(=O)NRR, —S(=O)2O—, —S(=O)2OH, —S(=O)2R, —OS(=O)2OR, —S(=O)2NR, —S(=O)R, —OP(=O)O2RR, —P(=O)O2RR, —P(=O)(O)2, —P(=O)(OH)2, —C(=O)R, —C(=O)X, —C(S)R, —C(O)OR, —C(O)O, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the terms "alkyl," "alkenyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylalcohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, thiazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The aryl, and heteroaryl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonythio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

The term "arylalkyl," as used herein, refers to a group comprising an aryl group attached to the parent molecular moiety through an alkyl group.

The term "carbonyl," as used herein, refers to "C(=O)".

As used herein, the term "cyclyl" refers to a nonaromatic 5-8 membered monocyclic, 8-12 membered bicyclic, or 11-14 membered tricyclic ring system, which can be saturated or partially unsaturated. Representative saturated cyclyl groups include, but are not limited to, cyclopropyl, cyclobutyl, cyclopentyl, cyclopentenyl, cyclohexyl, cyclohexenyl, cycloheptyl, cyclooctyl, and the like; while unsaturated cyclyl groups include cyclopentenyl and cyclohexenyl, and the like.

As used herein, the term "aryl" refers to an aromatic 5-8 membered monocyclic, 8-12 membered bicyclic, or 11-14 membered tricyclic ring system. Examples of aryl groups include phenyl, naphthyl and the like.

As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, thiazolyl, benzimidazolyl, pyrimidinyl, thiophenyl or thienyl, quinolinyl, indolyl, oxazolyl, and the like.

As used herein, the term "halogen" refers to iodine, bromine, chlorine, and fluorine.

As used herein, the terms "optionally substituted alkyl," "optionally substituted cyclyl," "optionally substituted heterocyclyl," "optionally substituted aryl," and "optionally substituted heteroaryl" means that, when substituted, at least one hydrogen atom in said alkyl, cyclyl, heterocylcyl, aryl, or heteroaryl is replaced with a substituent. In the case of an oxo substituent (=O) two hydrogen atoms are replaced. In this regard, substituents include oxo, halogen, alkyl, cyclyl, heterocyclyl, aryl, heteroaryl, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl, cyclyl, heterocyclyl, aryl or heterocycle, and each of said alkyl, cyclyl, heterocyclyl, aryl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

The terms "acyl," "carboxyl group," or "carbonyl group" are recognized in the art and can include such moieties as can be represented by the general formula:

wherein W is OR$^w$, N(R$^w$)$_2$, SR$^w$, or R$^w$, R$^w$ being hydrogen, alkyl, heteroalkyl, alkenyl, heteroalkenyl, alkynyl, heteroalkynyl, aryl, heteroaryl, heterocycle, substituted derivatives thereof, or a salt thereof. For example, when W is O-alkyl, the formula represents an "ester," and when W is OH, the formula represents a "carboxylic acid." When W is alkyl, the formula represents a "ketone" group, and when W is hydrogen, the formula represents an "aldehyde" group. Those of ordinary skill in the art will understand the use of such terms.

As used herein, the term "heterocyclyl" refers to a non-aromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. The heterocycle can include portions which are saturated or unsaturated. In some embodiments, the heterocycle may include two or more rings (e.g., cycloalkyls, cycloalkenyls, cycloalkynyls, aryls and/or heterocyclyls) in which two or more carbons are common to two adjoining rings, e.g., the rings are "fused rings." In some embodiments, the heterocycle may be a "bridged" ring, where rings are joined through non-adjacent atoms, e.g., three or more atoms are common to both rings. Each of the rings of the heterocycle may be optionally substituted. Examples of heterocyclyl groups include, for example, piperazinyl, pyrrolidinyl, dioxanyl, morpholinyl, tetrahydrofuranyl thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with substituents including, for example, halogen, aryl, heteroaryl, alkyl, heteroalkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, CF$_3$, CN, or the like.

As used herein, the term "substituted" is contemplated to include all permissible substituents of organic compounds, "permissible" being in the context of the chemical rules of valence known to those of ordinary skill in the art. In some cases, "substituted" refers to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic, fused, and bridged substituents of organic compounds. Illustrative substituents include, for example, those described herein. The permissible substituents can be one or more and the same or different for appropriate organic compounds. It is contemplated herein that heteroatoms such as nitrogen may have hydrogen substituents and/or any permissible substituents of organic compounds described herein which satisfy the valencies of the heteroatoms. This description is not intended to be limited in any manner by the permissible substituents of organic compounds.

Nucleic Acid Inhibitors of NNT Expression

In one embodiment, a nucleic acid inhibitor of NNT expression and/or activity is contemplated for use with the methods described herein, for example, through the use of RNA interference agents. The use of RNA interference agents are well within the abilities of one of skill in the art and are not described in detail herein. A brief summary of RNA interference practices is provided herein below.

RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. In one embodiment, the RNA is double stranded RNA (dsRNA). As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" can comprise an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the NNT sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. Therefore, one may initially screen the proposed siRNAs to avoid potential off-target silencing using the sequence identity analysis by any known sequence comparison methods, such as BLAST. siRNA sequences can also be chosen to maximize the uptake of the antisense (guide) strand of the siRNA into RISC and thereby maximize the ability of RISC to target human NNT mRNA for degradation. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function.

siRNA sequences to target NNT, can also be obtained commercially from e.g., INVITROGEN™, THERMO SCIENTIFIC™, ORIGENE™, among others.

Delivery of RNA Interfering Agents

Methods of delivering RNA interference agents, e.g., an siRNA, or vectors containing an RNA interference agent, to the target cells, e.g., melanocytes, skin cells, or other desired target cells, for uptake include injection of a composition containing the RNA interference agent, e.g., an siRNA, or directly contacting the cell, e.g., a melanocyte cell, with a composition comprising an RNA interference agent, e.g., an siRNA. In another embodiment, the RNA interference agent is administered topically. For topical administration it is further contemplated that the composition comprising the RNA interference agent will comprise a penetrating agent to facilitate intracellular delivery of the RNA agent.

The RNA interference agent is delivered in a pharmaceutically acceptable carrier. One or more RNA interference agent may be used simultaneously. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., melanocytes or other cells, inhibit annealing of single strands, stabilize single strands, or otherwise facilitate delivery to the target cell and increase inhibition of the target gene, e.g., NNT.

Methods of Determining Redox Status of a Cell

As described herein in the Examples section, there is a correlation between the reduction/oxidation (redox) status or state of e.g., melanocytes in skin and the degree of pigmentation (e.g., eumelanin expression). The redox status of a cell is determined, in part, by the level or amount of free radicals or antioxidants in the cell. Thus, to determine the redox status of a cell, one of skill in the art can determine the level of reactive oxygen species themselves (e.g., hydroxyl radical, hydrogen peroxide, superoxide), the level of intracellular antioxidants (e.g., glutathione) or the ratio of reduced/oxidized cell signaling molecules or redox pairs (e.g., reduced glutathione (GSH)/oxidized glutathione (GSSG) ratios; NAD(P)+/NAD(P)H ratios etc.). Such redox pairs provide an accurate representation of the reactive oxygen species in the cell.

For the methods described herein, a biological sample comprising at least one melanocyte is obtained and the redox status of the cell is determined using e.g., a method(s) as described below. NNT inhibitors decrease GSH/GSSG levels and increase reactive oxygen species (ROS) shortly after treatment of melanocytes or human skin. Without wishing to be bound by theory, this temporary increase in ROS is specific to mitochondria and melanosomes. This redox alteration in turn induces an increase in eumelanin and pigmentation of cells and human skin explants via decreasing cysteine stores, which are needed to form pheomelanin and by increasing tyrosinase protein stability. Without wishing to be bound by theory, eumelanin is the most potent known ROS scavenger and reduces the risk of melanoma and other cancers.

Measuring Reactive Oxygen Species (ROS)

In one embodiment, the redox status of a melanocyte is determined by measuring reactive oxygen species. Non-limiting examples of assays for measuring reactive oxygen species include DCFDA staining and MITOSOX™ staining of live cells.

DCFDA

In one embodiment, the cell permeant reagent 2',7'-dichlorofluorescin diacetate (DCFDA) is used to determine the redox status of a cell. DCFDA is a fluorogenic dye that measures hydroxyl, peroxyl and other reactive oxygen species (ROS) activity within the cell. After diffusion into the cell, DCFDA is deacetylated by cellular esterases to a non-fluorescent compound, which is later oxidized by ROS into 2',7'-dichlorofluorescein (DCF). DCF is a highly fluorescent compound which can be detected by fluorescence spectroscopy with maximum excitation and emission spectra of 495 nm and 529 nm respectively. Kits for using DCFDA are available commercially from e.g., ABCAM ("Cellular Reactive Oxygen Species Detection Assay Kit").

MITOSOX™ Mitochondrial ROS Staining

MITOSOX™ Red reagent is a fluorogenic dye specifically targeted to mitochondria in live cells. It is readily oxidized by superoxide but not by other reactive oxygen species or reactive nitrogen species. Oxidation of MITOSOX™ Red reagent by superoxide produces red fluorescence (absorption/emission maxima: ~510/580 nm). The production of superoxide by mitochondria can be visualized in fluorescence microscopy using the MITOSOX™ Red reagent. MITOSOX™ Red reagent permeates live cells where it selectively targets mitochondria. The oxidized product of MITOSOX™ is highly fluorescent upon binding to nucleic acid. In one embodiment, the MITOSOX Red Mitochondrial Superoxide Indicator is obtained commercially from LIFE TECHNOLOGIES.

NAD+/NADH Assays and NADP/NADPH Assays

Nicotinamide adenine dinucleotide (NAD), its phosphate counterpart (NADP) and its derivative compounds are essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda and Di Girolamo, EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). Recently, it has also been shown that NAD and its derivatives play an important role in transcriptional regulation (Lin and Guarente, Curr. Opin. Cell. Biol., (2003) 15, 241-246).

NAD+ or NADP can be detected by any means known in the art. In some embodiments, NAD+ or NADP is detected and/or measured using an enzyme linked assay, for example, by reconstituting the NAD biosynthesis pathway in vitro as described in e.g., PCT Publication No. WO2006/041624. In one embodiment, the assay is an enzyme-coupled fluorometric assay that can be used to measure NAD biosynthesis. In one embodiment, the enzyme-coupled reaction measures the fluorescence of NADH detected by a fluorometer following conversion of NAD to NADH by alcohol dehydrogenase.

Quantification of NAD+ and/or NADH (or NADP and/or NADPH) can include, for example, a determination of the relative amounts or concentration of NAD+ and/or NADH in the assay mixture. Quantifying NAD+ or NADH can be according to, for example, high performance liquid chromatography of NAD+ or autofluorescence of NADH, respectively.

Alcohol dehydrogenase and ethanol can be present in the reaction mixture employed by the method of identifying compounds that effect NAD biosynthesis. Where alcohol dehydrogenase and ethanol are present, detection or quantification of NADH can include, for example, detecting the fluorescence of the assay mixture and then correlating this fluorescence to the concentration of NADH produced in the assay mixture. Detection of the autofluorescence of NADH can be performed with, for example, a commercially available fluorometer. Alcohol dehydrogenase and ethanol can be present in the various embodiments that include NAD detection, NADH detection, quantification of NAD, quantification of NADH, and determinations of increases or decreases of NAD, NADH, or both.

In another embodiment, NAD+ or NADP can be detected and/or measured colorimetrically.

NAD+ can also be measured using an assay kit obtained commercially from e.g., ABCAM, MBL INTERNATIONAL, CAYMAN CHEMICALS, ABNOVA, SIGMA-ALDRICH, AAT BIOQUEST, among others. In one embodiment, NADP/NADPH ratios are determined by NADP/NADPH-GLO assay commercially available from PROMEGA.

In one embodiment, the NAD+/NADH or NADP/NADPH ratio of a biological sample comprising at least one melanocyte treated according to the methods described herein is reduced by at least 50% (e.g., at least 60%, at least 70%, at least 80%, at least 90%, at least 95%, at least 99% or more) compared to the NAD+/NADH or NADP/NADPH ratio of the biological sample prior to treatment.

In some embodiments, the NAD+/NADH or NADP/NADPH ratio in a treated sample is substantially similar to the control, untreated sample. Without wishing to be bound by theory, this is due to the localization of NNT in the mitochondrial membrane, and the effect on redox status occurs in a localized manner, therefore an overall change in cell redox status is not discernible. In such cases, it is preferable to measure eumelanin expression as an indicator of skin and/or hair pigmentation.

GSH/GSSG Assays

Glutathione is a peptide made from three amino acids: glutamic acid, cysteine and glycine. It is often present at a much higher concentration in the cell than other proteins and peptides. Glutathione can exist in multiple forms in a cell. The two forms most often considered to relate to the cell's redox state/potential are GSH and GSSG. GSH, the reduced form, occurs when glutathione is unbound to other molecules (Monostori et al. 2009. J. Chromatography B 877: 3331-3346). GSSG, the oxidized form, occurs when a disulfide bond exists between two glutathione molecules. GSH is often considered a first line of defense against oxidative damage and can remove active species from the cell and form GSSG. Since GSH and GSSG are related to each other through a simple oxidation/reduction reaction, they establish a redox state/potential within the cell. Further, since GSH and GSSG in total typically make up the highest redox couple in the cell, the determination of the amount of GSH and GSSG in a cell is usually performed, and the ratio of GSH to GSSG reported as a measure of the redox potential of the cell. Changes in the ratio of GSH and GSSG are often used as a measurement of oxidative damage in the cell.

While multiple methods exist for the measurement of GSH in a sample, the most commonly used is the combination of an enzyme, such as glutathione reductase with Ellman's reagent (Monostori et al. 2009) and chromatographic methods, e.g. HPLC methods (Monostori et al. 2009). These methods utilize several processing steps including acidification, protein removal by precipitation, neutralization, internal control addition and others before sample addition for glutathione measurement (Monostori et al. 2009).

Measurement of the GSSG level in samples can also be performed using a variety of methods. Several methods for determination of GSSG have been reported. A number of these methods calculate the level of GSSG in a sample by initially measuring the level of GSH and then measuring the level of GSH after reducing all of the GSSG to GSH (Monostori et al. 2009). The level of GSSG is then estimated by subtracting the amount of GSH found in the initial measurement of GSH from that of the level of GSH following reduction of GSSG to GSH.

Other methods for the measurement of GSSG require that GSH first be chemically modified in the sample to prevent it from giving a signal in the GSH measurement reaction. Then, the GSSG in the sample is reduced to GSH and, finally, the resulting GSH generated from GSSG is measured. In such cases, alkylating agents such as N-ethylmaleamide (NEM) are used to rapidly and irreversibly modify the GSH into a form that will not give signal in the GSH measurement reaction.

In one embodiment GSH/GSSG ratios are determined using the GSH/GSSG-GLO assay commercially available from PROMEGA.

In one embodiment, the ratio of GSH/GSSG in an untreated biological sample comprising at least one melanocyte is between 11 and 20; in other embodiments the ratio of GSH/GSSG in an untreated biological sample comprising at least one melanocyte is within the range of 12 to 20, between 13 to 20, between 14-20, between 15 to 20, between 16 to 20, between 17 to 20, between 18 to 20, between 19 to 20, between 12 to 14, between 12 to 15, between 12 to 16, between 12 to 17, between 12 to 18, or any range therein.

In one embodiment, the ratio of GSH/GSSG in a biological sample comprising at least one melanocyte treated with an agent that modifies redox status in a melanocyte (e.g., NNT inhibitor) is less than 10, less than 9, less than 8, less than 7, less than 6, less than 5, less than 4, less than 3, less than 2 or less than 1. In other embodiments, the ratio of GSH/GSSG in a biological sample comprising at least one melanocyte treated with an agent that modifies redox status in a melanocyte (e.g., NNT inhibitor) is within the ranges of 1 to 3, 1 to 4, 1 to 5, 1 to 7, 1 to 10, 3 to 5, 3 to 7, 3 to 10, 5 to 7, 5 to 10, 7 to 10, or ranges therein.

In one embodiment, the GSH/GSSG ratio of a biological sample comprising at least one melanocyte treated according to the methods described herein is reduced by at least 50% (e.g., at least 60%, at least 70%, at least 80%, at least 90%, at least 95%, at least 99% or more) compared to the GSH/GSSG ratio of the biological sample prior to treatment.

In some embodiments, the GSH/GSSG ratio in a treated sample is substantially similar to the control, untreated sample. Without wishing to be bound by theory, this is due to the localization of NNT in the mitochondrial membrane, and the effect on redox status occurs in a localized manner, therefore an overall change in cell redox status is not discernible. In such cases, it is preferable to measure eumelanin expression as an indicator of skin and/or hair pigmentation.

Cell Viability Measures

In one embodiment, the viability of a cell or the proliferation of a cell is determined using a bromodeoxyuridine (BrdU) assay. BrdU is a synthetic analog of thymidine that is commonly used in the detection of proliferating cells in living tissues. BrdU can be incorporated into the newly synthesized DNA of replicating cells (during the S phase of the cell cycle), substituting for thymidine during DNA replication. Antibodies specific for BrdU can then be used to detect the incorporated chemical, thus indicating cells that were actively replicating their DNA. BrdU assays are well known to those of skill in the art and are not described in detail herein. In some embodiments, an ATP=based measurement can be used (e.g., Cell Titer Glow™).

Eumelanin and/or NNT Expression Levels

In one embodiment, the expression of eumelanin is measured to determine or quantify skin pigmentation of a subject or a biological area of a subject. In another embodiment, the expression of NNT is measured to determine or quantify skin pigmentation of a subject or a biological area of a subject. In one embodiment, the expression of eumelanin is determined by measuring the optical density (O.D.) of the sample at e.g., 450 nm or HPLC measurements. Protein expression levels can be measured, e.g., using immunoassays such as Western blotting, dot blotting, ELISA, immunoPCR, immunoprecipitation, lateral flow immunoassay, radioimmunoassay and the like, or with proteomic detection methods which detect many proteins simultaneously, multidimensional gel electrophoresis, mass spectrometry based methods, or surface plasmon resonance techniques.

Antibodies directed against eumelanin, and/or NNT can be applied for disease diagnostics and monitoring efficacy of treatment. Such methods can be used to detect abnormalities or differences in the level of expression of eumelanin, and/or NNT, and/or the tissue, cellular, or subcellular location of the peptide. Generally, however, it will be the amount of eumelanin and/or NNT that is of primary interest. Antibodies to be used for protein analysis are widely available through commercial sources including ABCAM™ (Cambridge, Mass.), NEW ENGLAND BIOLABS™ (Ipswich, Mass.), SANTA CRUZ BIOTECHNOLOGIES™ (Santa Cruz, Calif.), and CELL SIGNALING™ (Danvers, Mass.), among others. Antibodies can also be raised against a polypeptide or portion of a polypeptide by methods known to those skilled in the art. While both polyclonal and monoclonal antibodies can be used in the methods described herein, it is preferred that a monoclonal antibody is used where conditions require increased specificity for a particular protein. Antibody manufacture methods are described, for example, in Harlow et al., 1988. The antibodies that recognize eumelanin and/or NNT may be any antibody variant, antibody derivative, bispecific molecule, human antibody, humanized antibody, monoclonal antibody, human monoclonal, and variants and antigen-binding fragments thereof. Conventional methods for immunohistochemistry are described in Harlow and Lane, 1988 and Ausbel et al, 1987.

In some embodiments, expression levels of eumelanin, and/or NNT can be determined by measuring the level of messenger RNA (mRNA) expression. Detection of mRNA expression is known by persons skilled in the art, and can comprise, for example PCR procedures, RT-PCR, Northern blot analysis, RNAse protection assay, etc. Nucleic acid and ribonucleic acid (RNA) molecules can be isolated from a particular biological sample using any of a number of procedures that are well-known in the art, the particular isolation procedure chosen being appropriate for the particular biological sample.

Primers or probes of use in the methods described herein include naturally occurring or recombinant single- or double-stranded nucleic acids or chemically synthesized nucleic acids. They may be labeled by nick translation, Klenow fill-in reaction, PCR or other methods known in the art. Probes useful in the methods described herein, their preparation and/or labeling are described in, for example Sambrook et al. (1989). A probe can be a polynucleotide of any length suitable for selective hybridization to a nucleic acid containing a polymorphic region of the invention. Length of the probe used will depend, in part, on the nature of the assay used and the hybridization conditions employed. In one embodiment, probes are labeled with two fluorescent dye molecules to form so-called "molecular beacons" (Tyagi, S. and Kramer, F. R., 1996). Such molecular beacons signal binding to a complementary nucleic acid sequence through relief of intramolecular fluorescence quenching between dyes bound to opposing ends on an oligonucleotide probe. A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

In some embodiments, the expression levels of eumelanin, and/or NNT are normalized to a control, such as a housekeeping gene. This is particularly useful for comparing levels of eumelanin and/or NNT amongst samples (e.g., between individuals, or between affected and unaffected regions etc). Suitable controls for normalizing expression levels of biomarkers are known to those of skill in the art. In certain embodiments, any gene or gene product can be used as a normalizing control, provided that the mRNA or protein is constitutively expressed, and is not differentially regulated in disease states (e.g., a hypopigmentation disorder). One of skill in the art can easily determine if a gene or gene product can be used as a normalizing marker by comparing the expression levels in samples taken at different time points from one individual, or among a plurality of samples taken from diseased and control populations. Typically, an appropriate normalization control marker will not fluctuate widely (e.g., less than 30%) among time points or among disease populations when assessed using an assay (e.g., a microarray).

In one embodiment, the expression level of eumelanin is determined by measuring the optical density of the sample at 450 nm (OD450). In some embodiments, the expression level of eumelanin is increased by at least 1%, at least 2%, at least 5%, at least 10% at least 11%, at least 12%, at least 13%, at least 14%, at least 15%, at least 16%, at least 17%, at least 18%, at least 19%, at least 20%, at least 30%, at least 40%, at least 50%, at least 60%, at least 70%, at least 80%, at least 90%, at least 1-fold, at least 1.5-fold, at least 2 fold, at least 5 fold, at least 10 fold, at least 100-fold, or more. It will be appreciated by one of skill in the art that very small changes in the percentage of eumelanin expression (e.g., 5%) can dramatically induce skin darkening (e.g., by 1-fold or higher). In one embodiment, an unknown agent for use with the methods described herein is screened from a library of candidate compounds using eumelanin levels (e.g., OD450) as an endpoint, thereby identifying an agent that enhances skin and hair pigmentation.

Reference Values

The terms "reference value," "reference level," "reference sample," and "reference" are used interchangeably herein and refer to the level of reactive oxygen species (ROS) in a known sample against which another sample (e.g., one obtained from a subject having hypopigmentation) is compared. A reference value is useful for determining e.g., the amount of ROS or the relative increase/decrease of reactive oxygen species in a biological sample as a marker of skin and/or hair pigmentation. A reference value serves as a reference level for comparison, such that samples can be normalized to an appropriate standard in order to infer the sensitivity of a subject to treatment with an agent that enhances skin and/or hair pigmentation.

In one embodiment, a biological standard is obtained at an earlier time point (e.g., prior to the onset of treatment as described herein) from the same individual that is to be tested or treated as described herein. In another embodiment, a biological standard is obtained from the same subject prior to or at the onset of treatment but is obtained from a region of skin and/or hair that lacks hypopigmentation. In such cases, the level of eumelanin or another measure described herein (e.g., NAD+/NADH ratios, GSH/GSSG ratios, etc) can be determined in an area unaffected by hypopigmentation with the aim of inducing pigmentation in the skin and/or hair affected by hypopigmentation to a degree substantially similar to the unaffected region.

Alternatively, a reference value can be obtained, for example, from a known biological sample from a different individual (e.g., not the individual being tested) that comprises e.g., reactive oxygen species within a specific range. A known sample can also be obtained by pooling samples from a plurality of like-pigmented individuals to produce a reference value or range of values over an averaged population, wherein a reference value represents an average level of skin and/or hair pigmentation (or ROS level) among a population of individuals (e.g., a population of individuals lacking a hypopigmentation disorder). One of skill in the art will appreciate that the level of reactive oxygen species etc. will need to be determined for sub-populations or groups of subjects with similar skin pigmentation, such as individuals from a particular ethnic group (e.g., African American vs. European vs. Asian ethnicity). Thus, the level of reactive oxygen species in a reference value obtained in this manner is representative of an average level of this marker in at least one general sub-population of individuals lacking a hypopigmentation disorder. An individual sample is compared to this population reference value by comparing e.g., reactive oxygen species from a biological sample relative to the population reference value.

One of skill in the art will appreciate that hypopigmentation can be easily diagnosed visually, by colorimeter, or by Wood's lamp, however such a measure is typically qualitative in nature. In one embodiment, a quantitative range of values for e.g., reactive oxygen species in e.g., an area or individual affected by hypopigmentation is determined. Provided that the number of individuals in each group is sufficient, one can define a range of reactive oxygen species values for each population. These values can be used to define cut-off points for selecting a therapy or for monitoring efficacy of treatment. Thus, one of skill in the art can determine the level of reactive oxygen species in the skin and compare the value to the ranges in each particular sub-population to aid in determining the status of disease, the recommended course of treatment, and monitoring the efficacy of a treatment. Such value ranges are analogous to e.g., HDL and LDL cholesterol levels detected clinically. For example, LDL levels below 100 mg/dL are considered optimal and do not require therapeutic intervention, while LDL levels above 190 mg/dL are considered 'very high' and will likely require some intervention. One of skill in the art can readily define similar parameters for the level of e.g., reactive oxygen species in a region or subject affected by hypopigmentation or a region or subject unaffected by hypopigmentation. These value ranges can be provided to clinicians, for example, on a chart, programmed into a PDA etc.

A standard comprising a reference value or range of values can also be synthesized. A known amount of e.g., reactive oxygen species (or a series of known amounts) can be prepared within the typical expression range for ROS that is observed in a general population. This method has an advantage of being able to compare the extent of disease in one or more individuals or affected regions. This method can also be useful for subjects who lack a prior sample to act as a reference value or for routine follow-up post-diagnosis. This type of method can also allow standardized tests to be performed among several clinics, institutions, or countries etc.

Pharmaceutically Acceptable Carriers

Provided herein are compositions that are useful for enhancing skin and/or hair pigmentation in a subject. In one embodiment, the composition is a pharmaceutical composition. The composition can comprise a therapeutically or prophylactically effective amount of an agent that modifies the reduction/oxidation status of at least one signaling molecule, such as nicotine adenine dinucleotide (NAD). As but one example, agents that modify the reduction/oxidation status of e.g., NAD are inhibitors of nicotinamide nucleotide transhydrogenase (NNT).

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions. In a preferred embodiment, the agent will be formulated for topical, subcutaneous or intradermal delivery.

The compositions described herein include, but are not limited to, therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic (e.g., allergenic) when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic compositions described herein can include pharmaceutically acceptable salts of the components therein.

Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. In one embodiment, the carrier is dimethyl sulphoxide (DMSO).

While any suitable carrier known to those of ordinary skill in the art can be employed in the pharmaceutical compositions of this invention, the type of carrier will vary depending on the mode of administration. Compositions can be formulated for any appropriate manner of administration, including for example, topical, intradermal, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. In a preferred embodiment, the compositions described herein are formulated for topical, subcutaneous, or intradermal delivery.

Biodegradable microspheres (e.g., polylactate polyglycolate) can also be employed as carriers for the pharmaceutical compositions of this invention. Suitable biodegradable microspheres are disclosed, for example, in U.S. Pat. Nos. 4,897,268 and 5,075,109. Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions as described herein can be formulated as a lyophilizate. Compounds can also be encapsulated within liposomes using well known technology. The compositions described herein can be administered as part of a sustained release formulation (i.e., a formulation such as a capsule or sponge that effects a slow release of compound following administration). Such formulations can generally be prepared using well known technology and administered by, for example, oral, rectal or subcutaneous implantation, or by implantation at the desired target site. Sustained-release formulations can contain a polypeptide, polynucleotide dispersed in a carrier matrix and/or contained within a reservoir surrounded by a rate controlling membrane. Carriers for use within such formulations are biocompatible, and can also be biodegradable; preferably the formulation provides a relatively constant level of active component release. The amount of active compound contained within a sustained release formulation depends upon the site of implantation, the rate and expected duration of release and the nature of the condition to be treated or prevented.

For use in medicine, the salts of the compounds as described herein refer to non-toxic "pharmaceutically acceptable salts." Other salts can, however, be useful in the preparation of compounds as described herein or of their pharmaceutically acceptable salts. Suitable pharmaceutically acceptable salts of the compounds include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds as described herein carry an acidic moiety, suitable pharmaceutically acceptable salts thereof can include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/ diphosphate, polygalacturonate, salicylate, stearate, sulfate, subacetate, succinate, tannate, tartrate, teoclate, tosylate, triethiodide and valerate.

Representative acids and bases which can be used in the preparation of pharmaceutically acceptable salts include the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (+−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

It will also be appreciated that certain compounds as described herein can exist in free form for treatment, or where appropriate, as a pharmaceutically acceptable derivative thereof. According to the compounds and assays described herein, a pharmaceutically acceptable derivative includes, but is not limited to, pharmaceutically acceptable salts, esters, salts of such esters, or a pro-drug or other adduct or derivative of a compound described herein, which upon administration to a patient in need thereof is capable of providing, directly or indirectly, a compound as otherwise described herein, or a metabolite or residue thereof.

Prodrugs and solvates of a compound as disclosed herein are also contemplated herein. The term "prodrug," as employed herein, denotes a compound that, upon administration to a subject, undergoes chemical conversion by metabolic or chemical processes to yield a compound described herein or a salt and/or solvate thereof. In general, such prodrugs can be functional derivatives of the compounds which are readily convertible in vivo into the required compound. Thus, in the methods and assays described herein, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Prodrugs of a compound as described herein, such as any NNT inhibitor compound can include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Balant et al., "Prodrugs for the improvement of drug absorption via different routes of administration", *Eur. J. Drug Metab. Pharmacokinet.*, 15(2): 143-53 (1990); Bundgaard H. "Improved drug delivery by the prodrug approach", *Controlled Drug Delivery* 17: 179-96 (1987), among others.

During any of the processes for preparation of the compounds as described herein, it may be necessary and/or desirable to protect sensitive or reactive groups on any of the molecules concerned. This can be achieved by means of conventional protecting groups, such as those described in e.g., Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups can be removed at a convenient subsequent stage using methods known from the art.

Various polymorphs of compounds as described herein can be prepared by crystallization of a small molecule under different conditions. Examples of different conditions are: using different commonly used solvents or their mixtures for crystallization; crystallization at different temperatures; and various modes of cooling, ranging from very fast to very slow cooling during crystallizations. Polymorphs can also be obtained by heating or melting the compound followed by gradual or fast cooling. The presence of polymorphs can be determined by IR spectroscopy, solid probe NMR spectroscopy, differential scanning calorimetry, powder X-ray diffraction or such other techniques.

The compounds as described herein can have asymmetric centers at any of the carbon atoms, including any one of the R substituents. Consequently, a compound as described herein can exist in enantiomeric or diastereomeric forms either in pure or substantially pure form or in mixtures thereof in all ratios. When diastereomeric or enantiomeric products are prepared, they can be separated by conventional methods for example, chromatographic or fractional crystallization. If mobile hydrogen atoms are present, the compositions described herein also encompass all tautomeric forms of a compound.

In one embodiment, the compositions described herein are formulated for topical administration. In some embodiments, the pharmaceutically acceptable topical formulations as contemplated herein comprise at least a compound as described herein and a penetration enhancing agent. The choice of topical formulation will depend on several factors, including the condition to be treated, the physicochemical characteristics of the administered compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. In certain exemplary embodiments, penetration agents for use with the compositions described herein include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decyl-methylsulfoxide, fatty acid esters (e.g., isopropyl myristate, methyl laurate, glycerol monooleate, and propylene glycol monooleate), dimethyl sulphoxide (DMSO) and N-methyl pyrrolidone.

In certain embodiments, the compositions can be in the form of ointments, pastes, creams, lotions, gels, powders, solutions, sprays, inhalants or patches. In certain exemplary embodiments, formulations of the compositions can further contain saturated or unsaturated fatty acids such as stearic acid, palmitic acid, oleic acid, palmito-oleic acid, cetyl or oleyl alcohols, stearic acid being particularly preferred. Such compositions can also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulation, eardrops, and eye drops are also contemplated herein.

It will also be appreciated that the compounds and pharmaceutical compositions described herein can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another biologically effective agent), or they may achieve different effects (e.g., control of any adverse effects).

Dosage and Administration

As used herein, the term "treatment" includes prophylaxis and therapy and includes cosmetic applications, which can be considered a prophylactic treatment. Prophylaxis or treatment can be accomplished by a single topical application or direct injection at a single time point or multiple time points. Administration can also be nearly simultaneous to multiple sites. Patients or subjects include mammals, such as human, bovine, equine, canine, feline, porcine, and ovine animals as well as other veterinary subjects. Preferably, the patients or subjects are human.

In one aspect, the methods described herein provide a method for enhancing skin and/or hair pigmentation in a subject. In another aspect, the methods described herein provide a method for treating a hypopigmentary disease or disorder. In one embodiment, the subject can be a mammal. In another embodiment, the mammal can be a human, although the approach is effective with respect to all mammals. The method comprises administering to the subject an effective amount of a pharmaceutical composition comprising an agent that modifies the reduction/oxidation status of a cell signaling molecule, such as an NNT inhibitor, in a pharmaceutically acceptable carrier. In some embodiments, the method comprises administering to the subject an effective amount of a pharmaceutical composition comprising e.g., an inhibitor of NNT, for example, a binding protein, such as an antibody or a peptide. In other embodiments, the inhibitor of NNT comprises a small molecule or an RNA interference molecule (e.g., siRNA, shRNA etc.).

The dosage range for the agent depends upon the potency, and includes amounts large enough to produce the desired effect, e.g., increased pigmentation of skin and/or hair. The dosage should not be so large as to cause unacceptable adverse side effects. Generally, the dosage will vary with the type of inhibitor (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 m/kg body weight to 30 m/kg body weight.

In some embodiments, the dose of an agent for use with the methods described herein (e.g., an NNT inhibitor, such as palmitoyl-CoA, 2,3-butanedione, or DCC) ranges from 1 µM to 1000 mM, 1 µM to 500 mM, from 1 µM to 400 mM, from 1 µM to 300 mM, from 1 µM to 250 mM, from 1 µM to 200 mM, from 1 µM to 150 mM, from 1 µM to 100 mM, from 1 µM to 75 mM, from 1 µM to 50 mM, from 1 µM to 25 mM, from 1 µM to 10 mM, from 1 µM to 1 mM, from 10 mM to 500 mM, from 50 µM to 500 mM, from 100 µM to 500 mM, from 1 mM to 500 mM, from 5 mM to 500 mM, from 25 mM to 500 mM, from 50 mM to 500 mM, from 75 mM to 500 mM, from 100 mM to 500 mM, from 200 mM to 500 mM, from 300 mM to 500 mM, from 400 mM-500 mM, from 10 mM to 100 mM, from 10 mM to 75 mM, from 20 mM to 100 mM, from 20 mM to 75 mM, from 30 mM to 75 mM, from 30 mM to 100 mM, from 15 mM to 60 mM, from 20 mM to 60 mM, from 30 mM to 60 mM, from 40 mM to 60 mM, and ranges therebetween.

It will be appreciated by those of skill in the art that light or very fair skin and/or hair is the most difficult to pigment and may require higher doses than would be necessary for less fair skin and/or hair. For example, subjects that are a Fitzpatrick scale Type I or Type II may require higher doses to enhance pigmentation than subjects that are a Type III or above. The Fitzpatrick scale is shown in the following table.

TABLE 1

Fitzpatrick Scale of Skin Color

| Fitzpatrick Type | Scores | Characteristics |
|---|---|---|
| I | 0-6 | Pale white; blond or red hair; blue eyes; freckles - Always burns, never tans |
| II | 7-13 | White; fair; blond or red hair; blue, green, or hazel eyes - Usually burns, tans minimally |
| III | 14-20 | Cream white; fair with any hair or eye color; quite common - Sometimes mild burn, tans uniformly |
| IV | 21-27 | Moderate brown; typical Mediterranean skin tone - Rarely burns, always tans well |
| V | 28-34 | Dark brown; Middle Eastern skin types - Very rarely burns, tans very easily |
| VI | 35-36 | Deeply pigmented dark brown to black - Never burns, tans very easily |

In some embodiments, the dose of 2,3-butanedione for use with the methods described herein are less than 1 mM, for example, less than 900 µM, less than 800 µM, less than 700 µM, less than 600 µM, less than 500 µM, less than 400 µM, less than 300 µM, less than 200 µM, less than 100 µM, less than 90 µM, less than 80 µM, less than 70 µM, less than 60 µM, less than 50 µM, less than 40 µM, less than 30 µM, less than 20 µM, less than 10 µM, less than 8 µM, less than 5 µM, less than 3 µM, less than 1 µM, less than 500 nM, less than 250 nM, less than 100 nM, less than 10 nM or even doses in the picomolar range.

Administration of the doses recited above can be repeated for a limited period of time. In some embodiments, the doses are given once a day, or multiple times a day, for example but not limited to three times a day. In another embodiment, the doses recited above are administered daily for several weeks, months, years or indefinitely. The duration of treatment depends upon the subject's clinical progress and responsiveness to therapy. Continuous, relatively low maintenance doses are contemplated after an initial higher therapeutic dose.

An effective amount is an amount of an agent that is sufficient to produce a statistically significant, measurable change in skin and/or hair pigmentation. Such effective amounts can be gauged in clinical trials as well as animal studies for a given agent.

In general, the compositions described herein are delivered directly to the skin and/or hair by topical, cutaneous, subcutaneous, or intradermal administration. Topical administration of a composition comprises applying the composition directly to the skin or hair, while intradermal injection (administration directly under the skin) can be used to achieve a high concentration of the agent at an affected area and can overcome penetration issues.

The agents or NNT inhibitors described herein can be formulated as an ointment, cream, lotion, solution, gel, oil, foam, liposomal formulation, or powder. One of skill in the art can choose one or more formulations for the agents described herein based on the agent or the subject's needs. Topical preparations can be mixed in a standard compounding pharmacy.

In one embodiment, the agents or NNT inhibitors described herein are formulated as an ointment. Ointments are oily and therefore are most appropriate when the skin needs lubrication or moisture. Ointments can be better than creams at delivering active ingredients into the skin. That is, a given concentration of a drug is more potent in an ointment than in a cream. Ointments are less irritating than creams and much less irritating than gels, lotions, and solutions for open wounds such as erosions or ulcers.

In another embodiment, the agents or NNT inhibitors described herein are formulated as a cream. Creams are emulsions of oil in water, meaning they are primarily water with an oil component. Creams are easy to apply and appear to vanish when rubbed into the skin. They are relatively nonirritating.

In another embodiment, the agents or NNT inhibitors described herein are formulated as a lotion. Lotions are similar to creams but contain more water. Lotions are actually suspensions of finely dispersed, powdered material in a base of water or oil and water. They are less effective than ointments, creams, and gels at delivering drugs and are considered of lower potency for a given drug concentration. However, lotions have a number of beneficial effects. They are easy to apply to hairy skin, and they are particularly useful for cooling or drying inflamed or oozing lesions, such as those caused by contact dermatitis, athlete's foot (tinea pedis), or jock itch (tinea cruris).

In another embodiment, the agents or NNT inhibitors described herein are formulated for delivery using a bath or soak. Baths and soaks can used when treatment must be applied to large areas of the body. This technique is most often used in the form of sitz baths for over-the-counter (OTC) treatments of mild skin problems such as hemorrhoids.

In another embodiment, the agents or NNT inhibitors described herein are formulated as a foam. Foams are aerosol preparations (liquids stored under pressure with a propellant so that the mixture can be dispensed) that use a base of alcohol or an emollient to soothe the skin. They are rapidly absorbed into the skin and are often used in hair-covered areas of the body.

In another embodiment, the agents or NNT inhibitors described herein are formulated as a solution. Solutions are liquids in which an agent as described herein is dissolved. The most commonly used liquids are alcohol, propylene glycol, polyethylene glycol, and plain water. Solutions are convenient to apply, especially for scalp disorders such as psoriasis or seborrheic dermatitis, or for enhancing the pigmentation of the hair. Non-limiting examples of solutions include Burow solution and Domeboro solution. In some embodiments, the solution is formulated for delivery of an NNT inhibitor to the eye.

In another embodiment, the agents or NNT inhibitors described herein are formulated as a powder. Powders are dried formulations of a composition that are used to protect areas where skin rubs against skin—for instance, between the toes or buttocks, in the armpits or groin, or under the breasts. Powders are used on skin that has been softened and damaged by moisture.

In another embodiment, the agents or NNT inhibitors described herein are formulated as a gel. Gels are water- or alcohol-based substances thickened without oil or fat. The skin does not absorb gels as well as it absorbs preparations containing oil or fat. Thus, they are often most effective for conditions that require slow absorption, such as acne, rosacea, and psoriasis of the scalp.

While topical or intradermal routes are most preferred, it is also contemplated herein that the agents can be delivered intravenously (by bolus or continuous infusion), orally, by inhalation, intranasally, intraperitoneally, intramuscularly, subcutaneously, intracavity, and can be delivered by peristaltic means, if desired, or by other means known by those skilled in the art. The agent can be administered systemically, if so desired.

In one embodiment, the agent is administered to a subject for an extended period of time. Sustained contact with a composition as described herein can be achieved by, for example, repeated administration of the composition over a period of time, such as one week, several weeks, one month or longer. More preferably, the pharmaceutically acceptable formulation used to administer the active compound provides sustained delivery, such as "slow release" of the agent to a subject. For example, the formulation can deliver the agent or composition for at least one, two, three, or four weeks after the pharmaceutically acceptable formulation is administered to the subject. In some embodiments, a subject to be treated in accordance with the methods described herein is treated with the active composition for at least 30 days (either by repeated administration or by use of a sustained delivery system, or both).

Preferred approaches for sustained delivery include use of a polymeric capsule, a minipump to deliver the formulation, a biodegradable implant, or implanted transgenic autologous cells (as described in e.g., U.S. Pat. No. 6,214,622). Implantable infusion pump systems (such as e.g., Infusaid™; see such as Zierski, J. et al, 1988; Kanoff, R. B., 1994) and osmotic pumps (sold by Alza Corporation™) are available in the art. Another mode of administration is via an implantable, externally programmable infusion pump. Suitable infusion pump systems and reservoir systems are also described in e.g., U.S. Pat. No. 5,368,562 by Blomquist and U.S. Pat. No. 4,731,058 by Doan, developed by Pharmacia Deltec™ Inc.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in an effective amount. The quantity to be administered and timing depends on the subject to be treated, capacity of the subject's system to utilize the active ingredient, and degree of therapeutic or cosmetic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., a melanocyte or keratinocyte). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration.

Alternatively, continuous intravenous infusion sufficient to maintain concentrations in the blood in the ranges specified for in vivo therapies are contemplated.

Efficacy of Treatment

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes enhancing skin and/or hair pigmentation or reducing or alleviating at least one adverse effect or symptom of a condition, disease or disorder associated with hypopigmentation. In other embodiments, "treating" further includes enhancing skin and/or hair pigmentation for cosmetic purposes, however one will readily appreciate that even such cosmetic applications can have prophylactic or therapeutic effects on skin again, sun-associated skin damage, DNA damage etc. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the agents described herein to a subject in order to enhance or increase skin and/or hair pigmentation (e.g., a subject having hypopigmentation). A patient who is being treated for a hypopigmentation disorder is one who a medical practitioner has diagnosed as having such a condition. Diagnosis can be by any suitable means, however diagnosis and monitoring will typically involve simple visual inspection by the subject themselves or a qualified physician. Quantitative measures of hypopigmentation can include: e.g., reactive oxygen species levels, NAD+/NADH ratios, GSH/GSSG ratios, cell viability, eumelanin expression etc.

The term "effective amount" as used herein refers to the amount of an agent or composition as described herein needed to enhance skin and/or hair pigmentation, and relates to a sufficient amount of pharmacological composition to provide the desired effect, i.e., increase skin darkening, increase eumelanin production, modify the ratio of reduced NADH to oxidized NAD+, etc. The term "effective amount" therefore refers to an amount of an agent using the methods as disclosed herein, that is sufficient to induce a particular effect (e.g., therapeutic or cosmetic) when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. An effective dose can be estimated initially from cell culture assays. Also, a dose can be formulated in animal models to achieve a circulating plasma concentration range that includes the IC50 (i.e., the concentration of the agent), which achieves a half-maximal inhibition of symptoms of hypopigmentation) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $4^{th}$ ed., J. Wiley & Sons (New York, N.Y. 2012); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 4th ed., Cold Spring Harbor Laboratory Press (Cold Spring Harbor, N. Y. 2012); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The present invention may be as defined in any one of the following numbered paragraphs 1. A method for enhancing pigmentation in a subject, the method comprising: administering a composition comprising an inhibitor of nicotinamide nucleotide transhydrogenase (NNT) to a subject or an area of the subject in need thereof, thereby enhancing pigmentation.
2. The method of paragraph 1, wherein the pigmentation is hair, skin, or eye pigmentation.
3. The method of paragraph 2, further comprising a step of measuring expression of eumelanin, cell viability, or assessing the degree of pigmentation in an area of the hair, skin, or eye to be treated.
4. The method of paragraph 3, wherein the step of measuring expression of eumelanin is performed by measuring OD 450 nm or HPLC.
5. The method of paragraph 3, wherein cell viability is measured using a BrdU assay or an ATP-based assay.
6. The method of any one of paragraphs 1-5, wherein administering the composition is used to treat and/or prevent a disease.
7. The method of any one of paragraphs 1-6, wherein administering the composition is used for cosmetic applications.
8. The method of any one of paragraphs 1-7, wherein the cosmetic application comprises sunless tanning, temporary tattooing, modification of eye color, or darkening of hair.
9. The method of paragraph 1, further comprising a step of determining redox status in a biological sample obtained from the subject.
10. The method of any one of paragraphs 1-9, wherein the redox status is determined by measuring reactive oxygen species (ROS) levels, NAD(P)+/NAD(P)H ratios, or GSH/GSSG ratios.
11. The method of any one of paragraphs 1-10, wherein the subject comprises at least one region of hypopigmentation.
12. The method of paragraph 3 or 10, wherein the levels of reactive oxygen species or eumelanin in a biological sample obtained from the subject following treatment with the NNT inhibitor are increased by at least 10% as compared to the levels of reactive oxygen species or eumelanin in a reference sample.
13. The method of paragraph 12, wherein the reference sample comprises a biological sample obtained from the same subject prior to treatment with the NNT inhibitor or an area of hair, skin, or eye to be treated.
14. The method of any one of paragraphs 1-13, wherein the inhibitor of NNT is administered topically, intradermally, or subcutaneously.
15. The method of any one of paragraphs 1-14, wherein the NNT inhibitor comprises palmitoyl CoA or a derivative thereof.
16. The method of any one of paragraphs 1-15, wherein the NNT inhibitor comprises N, N-Dicyclohexylcarbodiimide (DCC) or a derivative thereof.
17. The method of any one of paragraphs 1-16, wherein the NNT inhibitor comprises 2,3-butanedione or a derivative thereof.
18. The method of any one of paragraphs 1-17, wherein the NNT inhibitor modifies redox status in a melanocyte of the subject.
19. A method for enhancing skin or hair pigmentation in a subject, the method comprising administering a composition comprising an agent that modifies redox status in a melanocyte to a subject in need thereof.
20. The method of paragraph 19, further comprising a step of determining redox status in a biological sample obtained from the subject.
21. The method of paragraph 19, wherein the redox status is determined by measuring reactive oxygen species (ROS) levels, NAD+/NADH ratios, GSH/GSSG ratios, cell viability, or eumelanin expression.
22. The method of paragraph 21, wherein cell viability is measured using a BrdU assay.
23. The method of paragraph 21, wherein the ratio of reduced glutathione (GSH) to oxidized glutathione (GSSG) is decreased by at least 10% compared to a reference sample.
24. The method of paragraph 21, wherein the ratio of oxidized nicotine adenine dinucleotide (NAD+) to reduced nicotine adenine dinucleotide (NADH) is increased by at least 10% compared to a reference sample.
25. The method of paragraphs 21 or 23, wherein the GSH/GSSG ratio is less than 10 as determined using an assay comprising GSH/GSSG-GLO assay.
26. The method of any one of paragraphs 21, 23 or 25, wherein the GSH/GSSG ratio of melanocytes treated with the agent is reduced by at least 40% compared to the GSH/GSSG ratio of untreated melanocytes.

27. The method of paragraph 21, wherein the eumelanin expression is increased by at least 5% as measured using O.D. 450 nm.
28. A method for treating and/or preventing a lesion in a subject, the method comprising administering a composition comprising an inhibitor of nicotinamide nucleotide transhydrogenase (NNT) to a subject in need thereof, thereby treating or preventing the lesion in the subject.
29. The method of paragraph 28, wherein the lesion comprises a cancerous lesion.
30. The method of paragraph 28 or 29, wherein the cancerous lesion comprises melanoma.
31. The method of paragraph 28, 29, or 30, further comprising a step of assessing DNA damage in the lesion.
32. The method of any one of paragraphs 28-31, wherein the DNA damage in the lesion is assessed by measuring cyclobutane pyrimidine dimers (CPD) in the subject.
33. The method of any one of paragraphs 28-32, further comprising a step of measuring expression of eumelanin in the lesion or area to be treated.
34. The method of paragraph 33, wherein the step of measuring expression of eumelanin is performed by measuring OD 450 nm or HPLC.
35. The method of any one of paragraphs 28-34, wherein the composition is applied as a prophylactic to prevent formation of a lesion.
36. The method of any one of paragraphs 28-35, wherein the composition is applied to a discrete lesion.
37. The method of any one of paragraphs 28-36, wherein the inhibitor of NNT is administered topically, intradermally, or subcutaneously.
38. The method of any one of paragraphs 28-37, wherein the NNT inhibitor comprises palmitoyl CoA.
39. The method of any one of paragraphs 28-38, wherein the NNT inhibitor comprises N, N-Dicyclohexylcarbodiimide (DCC) or a derivative thereof.
40. The method of any one of paragraphs 28-39, wherein the NNT inhibitor comprises 2,3-butanedione.

EXAMPLES

Example 1

NNT, a Melanosomal Enzyme Regulating Melanin Synthesis In Vitro

The inventors performed electron microscopy of UACC 257 melanoma cells and primary melanocytes using a combination of primary rabbit anti-NNT-Antibody (Bioss) and a secondary anti-rabbit Gold-labeled antibody (data not shown). In addition, confocal microscopy of UACC 257 melanoma cells and primary melanocytes was performed (data not shown) using antibodies against NNT (Bioss) and HMB-45 (Dako North America, Inc.). Imaging of human primary melanocytes (WM26) and human melanoma cells (UACC257) showed co-localization of HMB-45 and NNT (WM26) and NNT indicating a close localization of melanosomes and NNT protein (data not shown).

Next, the inventors performed a study using liposomal siRNA-mediated knockdown of Nicotinamide Nucleotide Transhydrogenase (NNT), Tyrosinase (Tyr), and Micorophthalmia-associated Transcription Factor (MITF) in intermediately pigmented melanoma cells UACC257 and SK30 (liposomal siRNA delivery described by e.g., Haq et al., 2013). The protein levels of MITF, NNT, Tyr, Tyrosinase-related protein 1 and 2 (TRP1 and TRP2), beta-Actin and cAMP response element-binding protein (CREB) were determined via RT-PCR and Western Blot in UACC257 melanoma cells. (Western Blot and RT-PCR described by Haq et al., 2013). Eumelanin was detected by measuring the OD at 450 nm via a plate reader assay in UACC257 and SK30 melanoma cells (see Chen et al., 2014) (data not shown). Knockdown of intermediately pigmented human melanoma cells (SK30 and UACC257) with siNNT showed an increase of pigment as compared to siControl within 5 days after knockdown. These siNNT-mediated pigmentation changes were independent of mRNA changes in different genes involved in the pigmentation pathway (Tyr, TRP1, MITF). In addition, the siNNT-mediated pigmentation changes were independent of protein changes in different genes involved in the pigmentation pathway (TRP1, TRP2, pCREB, MITF) and showed a slight upregulation of Tyr protein. Without wishing to be bound by theory, these data indicate an increased protein stability (going along with an increased protein function) or the Tyr protein. Data from knockdown experiments of NNT by siNNT indicates that the levels of GSH did not change very much (data not shown). Without wishing to be bound by theory, this is likely due to local redox changes in melanosomes.

Additionally, without wishing to be bound by theory, the siNNT-mediated effect pigmentation effect is assumed to occur due to a decrease of intramelanosomal cysteine levels (e.g., GSH), driving a phenotypic switch from pheomelanin synthesis towards eumelanin synthesis and redox alterations driving an increased stability of the tyrosinase protein.

Example 2

NNT Inhibitors: Potent Players in the In Vivo Pigmentation Pathway

B6.Cg-MITF$^{Mi-wh}$+/−"grey" and Mc1re/e, "red" mice were identified to have a 7-exon deletion in their NNT genome (resulting in a dysfunctional NNT protein, see e.g., Freeman et al, 2006). These mice were compared to NNT wild-type (WT) controls in order to observe phenotypical differences in their fur and skin pigmentation. These mice were not treated with any drug. In both mouse models, animals displaying a dysfunctional NNT protein have darker pigmentation in their fur than their heterozygous (NNT+/−) and wild-type counterparts (NNT+/+) (data not shown). Without wishing to be bound by theory, the color differences (grey fur vs. red fur) observed is due to natural differences of the NNT protein. In addition, the ears of MiWhite+/− mice (NNT+/+vs. NNT−/−) were investigated via H&E staining and increased pigmentation was observed both macroscopically and microscopically in NNT−/− mice vs. the NNT+/+ mice (data not shown).

NNT inhibitors (N,N-Dicyclohexylcarbodiimide (DCC), 2,3-Butanedione, Palmitoyl-CoA) (Moody et al. Eur J Biochem. 1972 Dec. 18; 31:496-504; Rydstrom et al., Eur J Biochem. (1972)) were dissolved in DMSO at different concentrations (500 nM to 50 mM) and applied topically (2x/d for 5 days in a row) on human skin explants and human skin was observed for pigmentation changes via visual inspection staining procedures (e.g., Fontana Masson and HPLC measurements).

Human skin explants obtained from subjects undergoing abdominoplasty were defatted and grown on 2% agar plates for 10 days. These explants were treated topically or intradermally with NNT inhibitors. Skin explants were observed for pigmentation changes via visual inspection and Fontana-Masson staining.

NNT inhibitors decrease GSH/GSSG levels (without inducing cytotoxicity) and hereby induce pigmentation (shown by inspection and measuring the OD at 405 nm) in UACC257 and SK30 melanoma cells. Topical treatment with NNT inhibitors showed a dose and time dependent increase of pigmentation of melanoma cells and human skin explants of different donors observed by inspection, OD450 measurements, and Fontana-Masson staining.

Next, nude mice were engrafted with human skin and were treated for 12 days once a day with the NNT inhibitor DCC. This treatment induced pigmentation of hair of human skin and hair grafts in nude mice as observed by clinical inspection and microscopic analysis.

Example 3

NNT Inhibitors

Three different NNT inhibitors were tested for efficacy and toxicity in melanocytes and melanoma cells. Table 2 shows $IC_{50}$ values in uM for the NNT inhibitors: DCC, Palmitoyl-CoA and 2,3-Butanedione showing that the inhibitors have no significant toxicity in an in vitro system. Toxicity measured via ATP-based assays (Cell titer glow) 2 days after start of treatment.

TABLE 2

$IC_{50}$ values for NNT inhibitors

| $IC_{50}$ (uM) | Melano-cytes 1 | Melano-cytes 2 | Dermal Fibroblasts | Keratino-cytes |
|---|---|---|---|---|
| DCC | >10 | >10 | >10 | >10 |
| Palmitoyl-CoA | >10 | >10 | >10 | >10 |
| 2,3 Butanedione | >10 | >10 | >10 | >10 |

Skin patches corresponding to three different Fitzpatrick skin colors (light-Type I-II; intermediate-Type III-IV; dark-Type V-VI) were treated with 2,3-butanedione once per day for five consecutive days with the following doses: 1.2 µM, 5.8 µM, 11.5 µM, 1.15 mM, 5.8 mM, 11.5 mM, 57.5 mM, 115 mM, 575 mM, 1.15 M, 5.75M, and 11.5 M. Visible changes in skin pigmentation were observed at the lowest dose (1.2 µM) in all three skin types as compared to an untreated control and a DMSO treated control, indicating that very low doses can be used to increase skin pigmentation in any skin type. It will be appreciated that even lower doses of NNT inhibitors can be used in subjects having higher Fitzpatrick scores (Types V-VI) as such skin coloring is more readily pigmented in general.

Microscopic analysis of skin patches treated with 50 mM 2,3, butanedione and control patches treated with 30% PEG/ethanol using Fontana Masson staining indicates that the increase in skin pigmentation observed visually in the 2,3-butanedione treated patches is due to an increase in eumelanin expression at the microscopic level (data not shown). In addition, H&E staining was performed and no inflammation was observed in either control or NNT inhibitor treated patches (FIG. 21B).

In addition, skin patches (Fitzpatrick Type II) were topically treated for 4 days with 2,3 butane-dione at the following concentrations: 0.4% w/v (~47 mM), 0.8% w/v, 1.6% w/v, 3.12% w/v, 6.25% w/v, 12.5% w/v, and 25% w/v. The lowest concentration of 2,3-butanedione produced pigmentation that was darker than the pigmentation induced by a one-time UV-B treatment at 150 mJ/cm$^2$ (UV data not shown).

Example 4

NNT Inhibitors Protect from DNA Damage

Cyclobutane dimer (CPD) staining was performed on human skin treated with 50 mM 2,3butanedione for 5 consecutive days (treatment once per day) as a marker to assess DNA damage in the skin samples. On the fifth day, skin was irradiated with 1000 mJ/cm$^2$ UVB (equivalent to approximately 3 h in the sun at equatorial areas). In the absence of UV radiation exposure, application of 50 mM 2,3 butanedione caused a decrease in CPD formation in the human skin sample as compared to a DMSO treated control. In addition, 2, 3, butanedione was applied to skin that was then exposed to UVB radiation and a decrease in CPD was observed as compared to the DMSO+UVB control treated samples. These data indicate a protective role for 2,3BD from UVB-induced CPD damage, which is well known to cause carcinogenesis and melanoma development. These data further indicate that NNT inhibitors, such as 2,3-butanedione, can treat or prevent melanoma by decreasing and/or preventing formation of DNA damage.

REFERENCES

Cardiff et al., Hematoxylin and Eosin Staining of Tissue and Cell Sections, *Cold Spring Harb Protoc;* 2014

Chen et al., Hispolon Decreases Melanin Production and Induces Apoptosis in Melanoma Cells through the Down-regulation of Tyrosinase and Microphthalmia-Associated Transcription Factor (MITF) Expressions and the Activation of Caspase-3, -8 and -9. Int J Mol Sci. January 2014; 15(1): 1201-1215.

Freeman H C, Hugill A, Dear N T, Ashcroft F M, Cox R D. 2006. Deletion of Nicotinamide Nucleotide Transhydrogenase: A New Quantitative Trait Locus Accounting for Glucose Intolerance in C57BL/6J Mice. *Diabetes* 55(7): 2153-6.

Haq et al., BCL2A1 is a lineage-specific antiapoptotic melanoma oncogene that confers resistance to BRAF inhibition. Proc Natl Acad Sci USA. Mar. 12, 2013; 110(11): 4321-4326.

Jemal A, Devesa S S, Hartge P, Tucker M A (2001) Recent trends in cutaneous melanoma incidence among whites in the United States. *J Natl Cancer Inst.* 93: 678-83

Mitra D, Luo X, Morgan A, Wang J, Hoang M P, Lo J, Guerrero C R, Lennerz J K, Mihm M C, Wargo J A, Robinson K C, Devi S P, Vanover J C, D'Orazio J A, McMahon M, Bosenberg M W, Haigis K M, Haber D A, Wang Y, Fisher D E. (2012) An ultraviolet-radiation-independent pathway to melanoma carcinogenesis in the red hair/fair skin background. Nature. 15; 491:449-53

Tada M et al., J Clin Biochem Nutr. May 2010; 46(3): 224-228. Scavenging or Quenching Effect of Melanin on Superoxide Anion and Singlet Oxygen

The invention claimed is:

1. A method for enhancing pigmentation in a subject, the method comprising: administering topically, intradermally or subcutaneously a composition comprising an inhibitor of nicotinamide nucleotide transhydrogenase (NNT) to a subject or an area of the subject in need thereof, thereby enhancing pigmentation.

2. The method of claim 1, wherein the pigmentation is hair, skin, or eye pigmentation.

3. The method of claim 2, further comprising a step of measuring expression of eumelanin, cell viability, or assessing the degree of pigmentation in an area of the hair, skin, or eye to be treated.

4. The method of claim 1, wherein administering the composition is used to treat a hypopigmentation disorder, wherein the hypopigmentation disorder comprises existing melanocytes.

5. The method of claim 1, wherein administering the composition is used for cosmetic applications.

6. The method of claim 5, wherein the cosmetic application comprises sunless tanning, temporary tattooing, modification of eye color, or darkening of hair.

7. The method of claim 1, wherein the subject comprises at least one region of hypopigmentation.

8. The method of claim 1, wherein the NNT inhibitor comprises palmitoyl CoA, N, N-Dicyclohexylcarbodiimide (DCC), or 2,3-butanedione.

* * * * *